(12) United States Patent
Neustadter et al.

(10) Patent No.: US 8,239,002 B2
(45) Date of Patent: Aug. 7, 2012

(54) GUIDING A TOOL FOR MEDICAL TREATMENT BY DETECTING A SOURCE OF RADIOACTIVITY

(75) Inventors: David Maier Neustadter, Netanya (IL); Giora Kornblau, Binyamina (IL)

(73) Assignee: Novatek Medical Ltd., Yokneam (IL)

( * ) Notice: Subject to any disclaimer, the term of this patent is extended or adjusted under 35 U.S.C. 154(b) by 1340 days.

(21) Appl. No.: 11/463,664

(22) Filed: Aug. 10, 2006

(65) Prior Publication Data

US 2007/0055144 A1 Mar. 8, 2007

Related U.S. Application Data

(63) Continuation-in-part of application No. PCT/IL2005/000871, filed on Aug. 11, 2005, and a continuation-in-part of application No. PCT/IL2005/001101, filed on Oct. 19, 2005.

(60) Provisional application No. 60/773,931, filed on Feb. 16, 2006, provisional application No. 60/804,178, filed on Jun. 8, 2006, provisional application No. 60/773,930, filed on Feb. 16, 2006, provisional application No. 60/600,725, filed on Aug. 12, 2004, provisional application No. 60/619,792, filed on Oct. 19, 2004, provisional application No. 60/619,897, filed on Oct. 19, 2004, provisional application No. 60/619,898, filed on Oct. 19, 2004.

(51) Int. Cl.
*G01T 1/00* (2006.01)
(52) U.S. Cl. ............. 600/424; 250/303; 250/491.1; 600/436
(58) Field of Classification Search ............ 600/424, 600/431, 436; 250/302–303
See application file for complete search history.

(56) References Cited

U.S. PATENT DOCUMENTS

| | | | |
|---|---|---|---|
| 3,777,148 A | 12/1973 | Miraldi | |
| 3,794,840 A | 2/1974 | Scott | |
| 3,951,550 A | 4/1976 | Slick | |
| 4,096,862 A | 6/1978 | DeLuca | |
| 4,123,654 A | 10/1978 | Reiss et al. | |
| 4,193,689 A | 3/1980 | Reymond et al. | |
| 4,209,700 A | 6/1980 | Stoddart | |
| 4,215,694 A | 8/1980 | Isakov et al. | |

(Continued)

FOREIGN PATENT DOCUMENTS

CN 1469720 1/2004

(Continued)

OTHER PUBLICATIONS

Kirsch et al. "Real Time Tracking of Tumor Positions for Precision Irradiation", Car'98, Computer Assisted Radiology and Surgery, Proceedings of the International Congress and Exhibition, Proceedings of the International Symposium on Computer Assisted Radiology and Surgery, p. 262-264, 1998.

(Continued)

*Primary Examiner* — Jacqueline Cheng
(74) *Attorney, Agent, or Firm* — Finnegan, Henderson, Farabow, Garrett & Dunner, L.L.P.

(57) ABSTRACT

Systems and methods disclosed provide for guiding a tool using a source of radioactivity. The method includes implanting a source of radioactivity at a position having a geometric relationship to a target tissue, determining at least an indication of a location of the source using at least one radioactivity detecting position sensor, and positioning a tool at a desired relative location with respect to the target tissue based on the determined location.

54 Claims, 12 Drawing Sheets

U.S. PATENT DOCUMENTS

| | | | |
|---|---|---|---|
| 4,243,652 A | 1/1981 | Francis | |
| 4,250,392 A | 2/1981 | Leask et al. | |
| 4,636,380 A | 1/1987 | Wong | |
| 4,755,680 A | 7/1988 | Logan | |
| 4,782,840 A | 11/1988 | Martin, Jr. et al. | |
| 4,857,729 A | 8/1989 | Gadeken et al. | |
| 4,944,754 A | 7/1990 | Linkow | |
| 4,959,547 A | 9/1990 | Carroll et al. | |
| 5,114,401 A | 5/1992 | Stuart et al. | |
| 5,170,055 A | 12/1992 | Carroll et al. | |
| 5,207,223 A | 5/1993 | Adler | |
| 5,211,165 A | 5/1993 | Dumoulin et al. | |
| 5,342,283 A | 8/1994 | Good | |
| 5,344,452 A | 9/1994 | Lemperle | |
| 5,345,084 A | 9/1994 | Byrd | |
| 5,460,592 A | 10/1995 | Langton et al. | |
| 5,665,970 A | 9/1997 | Kronenberg et al. | |
| 5,694,933 A | 12/1997 | Madden et al. | |
| 5,707,332 A | 1/1998 | Weinberger | |
| 5,740,808 A | 4/1998 | Panescu et al. | |
| 5,813,985 A | 9/1998 | Carroll | |
| 5,846,513 A | 12/1998 | Carroll et al. | |
| 5,848,967 A | 12/1998 | Cosman | |
| 5,933,517 A | 8/1999 | Grangeat et al. | |
| 5,938,602 A | 8/1999 | Lloyd | |
| 5,961,457 A | 10/1999 | Raylman et al. | |
| 5,961,458 A | 10/1999 | Carroll | |
| 5,987,350 A | 11/1999 | Thurston | |
| 6,016,439 A | 1/2000 | Acker | |
| 6,033,721 A | 3/2000 | Nassuphis | |
| 6,068,623 A | 5/2000 | Zadno-Azizi et al. | |
| 6,100,530 A | 8/2000 | Kronenberg et al. | |
| 6,188,355 B1 | 2/2001 | Gilboa | |
| 6,230,038 B1 | 5/2001 | Von Gutfeld et al. | |
| 6,261,243 B1 | 7/2001 | Burney et al. | |
| 6,264,599 B1 | 7/2001 | Slater et al. | |
| 6,275,724 B1 | 8/2001 | Dickinson et al. | |
| 6,332,089 B1 | 12/2001 | Acker et al. | |
| 6,363,940 B1 | 4/2002 | Krag | |
| 6,371,904 B1 | 4/2002 | Sirimanne | |
| 6,380,732 B1 | 4/2002 | Gilboa | |
| 6,402,677 B1 | 6/2002 | Jacobs | |
| 6,419,621 B1 | 7/2002 | Sioshansi et al. | |
| 6,427,314 B1 | 8/2002 | Acker | |
| 6,436,026 B1 | 8/2002 | Sioshansi et al. | |
| 6,455,856 B1 | 9/2002 | Gagnon | |
| 6,496,717 B2 | 12/2002 | Cox et al. | |
| 6,510,336 B1 | 1/2003 | Daghighian et al. | |
| 6,558,612 B1 | 5/2003 | Hubbard | |
| 6,580,938 B1 | 6/2003 | Acker | |
| 6,593,884 B1 | 7/2003 | Gilboa et al. | |
| 6,603,124 B2 | 8/2003 | Maublant | |
| 6,618,612 B1 | 9/2003 | Acker et al. | |
| 6,675,810 B2 | 1/2004 | Krag | |
| 6,690,963 B2 | 2/2004 | Ben-Haim et al. | |
| 6,696,686 B1 | 2/2004 | Wainer et al. | |
| 6,698,433 B2 | 3/2004 | Krag | |
| 6,711,429 B1 | 3/2004 | Gilboa et al. | |
| 6,749,555 B1 | 6/2004 | Winkler et al. | |
| 6,750,020 B2* | 6/2004 | Shuber | 435/6 |
| 6,751,492 B2 | 6/2004 | Ben-Haim | |
| 6,788,967 B2 | 9/2004 | Ben-Haim et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,847,838 B1 | 1/2005 | Macey et al. | |
| 6,889,833 B2 | 5/2005 | Seiler et al. | |
| 6,918,919 B2 | 7/2005 | Krag | |
| 6,920,347 B2 | 7/2005 | Simon et al. | |
| 6,937,696 B1* | 8/2005 | Mostafavi | 378/95 |
| 6,977,504 B2 | 12/2005 | Wright et al. | |
| 7,047,063 B2 | 5/2006 | Burbank et al. | |
| 7,066,924 B1 | 6/2006 | Garibaldi et al. | |
| 7,247,160 B2 | 7/2007 | Seiler et al. | |
| 7,289,839 B2 | 10/2007 | Dimmer et al. | |
| 7,407,054 B2 | 8/2008 | Seiler et al. | |
| 7,684,849 B2 | 3/2010 | Wright et al. | |
| 2001/0005930 A1 | 7/2001 | Coniglione | |
| 2002/0058853 A1 | 5/2002 | Kaplan | |
| 2002/0061298 A1* | 5/2002 | Coffey et al. | 424/93.21 |
| 2002/0077533 A1 | 6/2002 | Bieger et al. | |
| 2002/0087078 A1 | 7/2002 | Cox et al. | |
| 2002/0193685 A1 | 12/2002 | Mate et al. | |
| 2003/0036700 A1* | 2/2003 | Weinberg | 600/436 |
| 2003/0088140 A1 | 5/2003 | Terwilliger et al. | |
| 2003/0111611 A1 | 6/2003 | Maublant | |
| 2003/0192557 A1* | 10/2003 | Krag et al. | 128/898 |
| 2004/0015075 A1* | 1/2004 | Kimchy et al. | 600/424 |
| 2004/0034297 A1 | 2/2004 | Darrow et al. | |
| 2004/0037394 A1 | 2/2004 | Kuroda et al. | |
| 2004/0054248 A1 | 3/2004 | Kimchy | |
| 2004/0068157 A1 | 4/2004 | Gellman et al. | |
| 2004/0073107 A1 | 4/2004 | Sioshansi et al. | |
| 2004/0116767 A1 | 6/2004 | Lebovic et al. | |
| 2004/0199072 A1 | 10/2004 | Sprouse et al. | |
| 2004/0236213 A1 | 11/2004 | Jones et al. | |
| 2005/0010099 A1 | 1/2005 | Raabe et al. | |
| 2005/0027196 A1 | 2/2005 | Fitzgerald | |
| 2005/0054910 A1 | 3/2005 | Tremblay et al. | |
| 2005/0055174 A1 | 3/2005 | David et al. | |
| 2005/0085717 A1 | 4/2005 | Shahidi | |
| 2005/0197564 A1 | 9/2005 | Dempsey | |
| 2005/0245814 A1 | 11/2005 | Anderson et al. | |
| 2005/0261570 A1 | 11/2005 | Mate et al. | |
| 2007/0055090 A1 | 3/2007 | Neustadter et al. | |
| 2007/0205373 A1 | 9/2007 | Kornblau et al. | |
| 2007/0265491 A1 | 11/2007 | Krag et al. | |
| 2008/0262473 A1 | 10/2008 | Kornblau et al. | |
| 2009/0127459 A1 | 5/2009 | Neustadter et al. | |
| 2009/0131734 A1 | 5/2009 | Neustadter et al. | |

FOREIGN PATENT DOCUMENTS

| | | |
|---|---|---|
| EP | 0273257 | 7/1988 |
| EP | 0466681 | 1/1992 |
| EP | 0531081 | 3/1993 |
| EP | 0993843 | 4/2000 |
| EP | 1034738 | 9/2000 |
| EP | 1060764 | 12/2000 |
| FR | 1561351 | 3/1969 |
| GB | 2330263 | 4/1999 |
| JP | 01-288250 | 11/1989 |
| WO | WO 97/29699 | 8/1997 |
| WO | WO 97/29700 | 8/1997 |
| WO | WO 99/21615 | 5/1999 |
| WO | WO 99/35966 | 7/1999 |
| WO | WO 00/24332 | 5/2000 |
| WO | WO 00/57923 | 10/2000 |
| WO | WO 00/71204 | 11/2000 |
| WO | WO 01/30447 | 5/2001 |
| WO | WO 01/54765 | 8/2001 |
| WO | WO 01/87409 | 11/2001 |
| WO | WO 02/16965 | 2/2002 |
| WO | WO 02/39142 | 5/2002 |
| WO | WO 02/39917 | 5/2002 |
| WO | WO 02/39918 | 5/2002 |
| WO | WO 02/078785 | 10/2002 |
| WO | WO 03/011161 | 2/2003 |
| WO | WO 03/032837 | 4/2003 |
| WO | WO 2004/026111 | 4/2004 |
| WO | WO 2006/004542 | 1/2006 |
| WO | WO 2006/016368 | 2/2006 |
| WO | WO 2006/043276 | 4/2006 |
| WO | WO 2007/017846 | 2/2007 |
| WO | WO 2007/017847 | 2/2007 |
| WO | WO 2007/094001 | 8/2007 |
| WO | WO 2007/094002 | 8/2007 |

OTHER PUBLICATIONS

Communication Relating to the Results of the Partial International Search Dated Jan. 7, 2008 From the International Searching Authority Re.: Application No. PCT/IL2007/000214.

International Preliminary Report on Patentability Dated May 9, 2007 From the International Preliminary Examining Authority Re.: Application No. PCT/IL05/01101.

International Preliminary Report on Patentability Dated Apr. 12, 2007 From the International Bureau of WIPO Re.: Application No. PCT/IL2005/000871.
International Preliminary Report on Patentability Dated Feb. 21, 2008 From the International Preliminary Examining Authority Re.: Application No. PCT/IB2006/052770.
International Preliminary Report on Patentability Dated Nov. 27, 2007 From the International Preliminary Examining Authority Re.: Application No. PCT/IB2006/052771.
International Preliminary Report on Patentability Dated Aug. 28, 2008 From the International Bureau of WIPO Re.: Application No. PCT/IL2007/000215.
International Preliminary Report on Patentability Dated Aug. 26, 2008 From the International Preliminary Examining Authority Re.: Application No. PCT/IL2007/000214.
Search Report.
Corrected International Search Report Dated Sep. 11, 2007 From the International Searching Authority Re.: Application No. PCT/IB2006/052770.
Examination Report Dated Oct. 27, 2009 From the Instituto Mexicano de la Propriedad Industrial Re.: Application No. MX/a/2007/001783 and Its Summary in English.
International Preliminary Report on Patentability Dated Oct. 7, 2009 From the International Preliminary Examining Authority Re.: Application No. PCT/IL05/00871.
Official Action Dated Nov. 5, 2009 From the US Patent and Trademark Office Re.: U.S. Appl. No. 10/599,963.
Amendment in Response to Restriction Requirement Dated Nov. 16, 2009 From the US Patent and Trademark Office Re.: U.S. Appl. No. 11/635,441.
Official Action Dated Oct. 29, 2009 From the US Patent and Trademark Office Re.: U.S. Appl. No. 11/463,659.
Preliminary Amendment Dated Sep. 26, 2008 From the US Patent and Trademark Office Re.: U.S. Appl. No. 11/635,441.
Second Preliminary Amendment Dated Jul. 20, 2007 Re.: U.S. Appl. No. 11/635,441.
Translation of Office Action Dated Aug. 7, 2009 From the State Intellectual Property Office of the People's Republic of China Re.: Application No. 200580034274.1.
Hyun an et al. "Optimization of a Table-Top Compton Camera System by Monte Carlo Simulation", Nuclear Instruments and Methods in Physics Research A, 580: 169-172, 2007.
Singh "An Electronically Collimated gamma Camera for single Photon Emission Computed Tomography. Part I: Theoretical Considerations and Design Criteria", Medical Physics, 10: 421-427, 1983.
"Calypso® 4D Localisation System-GPS for the Body®" in Calypso® Medical: Products& Technology—The Problem, downloaded from <http:// calypsomedical.com/products/> on Dec. 12, 2002.
Lengyel J. et al., "Three-dimensional reconstruction and volume rendering of intravascular ultrasound slices imaged on a curved arterial path"; in Nicholas Ayache, editor, Computer Vision, Virtual Reality and Robotics in Medicine, Lecture Notes in Computer Science. Springer-Verlag, Apr. 1995.
International Search Report Dated Jan. 3, 2007 From the International Searching Authority Re.: Application No. PCT/IB2006/052771.
International Search Report Dated Mar. 6, 2007 From the International Searching Authority Re.: Application No. PCT/IL05/00871.
International Search Report Dated Jan. 7, 2008 From the International Searching Authority Re.: Application No. PCT/IL2007/000215.
International Search Report Dated Sep. 10, 2007 From the International Searching Authority Re.: Application No. PCT/IB2006/052770.
International Search Report Dated Feb. 29, 2008 From the International Searching Authority Re.: Application No. PCT/IL2007/000214.
International Search Report Dated May 30, 2006 From the International Searching Authority Re.: Application No. PCT/IL05/01101.
Official Action Dated Jun. 24, 2009 From the US Patent and Trademark Office Re.: U.S. Appl. No. 10/599,963.
Written Opinion Dated Jan. 3, 2007 From the International Searching Authority Re.: Application No. PCT/IB2006/052771.
Written Opinion Dated Mar. 6, 2007 From the International Searching Authority Re.: Application No. PCT/IL05/00871.
Written Opinion Dated Jan. 7, 2008 From the International Searching Authority Re.: Application No. PCT/IL2007/000215.
Written Opinion Dated Sep. 10, 2007 From the International Searching Authority Re.: Application No. PCT/IB2006/052770.
Written Opinion Dated Feb. 29, 2008 From the International Searching Authority Re.: Application No. PCT/IL2007/000214.
Office Action dated Jan. 12, 2011, in the Israel Patent Office for Israel Application No. 207209 including excerpts from US-2003/0111611 (6 pages, including translation).
Office Action dated Jan. 16, 2011, in the Israel Patent Office for Israel Application No. 207210 including excerpts from US 3,951,550 (7 pages, including translation).
USPTO Final Rejection dated Feb. 3, 2011, in U.S. Appl. No. 11/635,441 to Krag et al. (13 pages).
USPTO Office Action dated Feb. 18, 2011, in co-pending U.S. Appl. No. 11/463,659 (8 pages).
Extended European Search Report and Written Opinion dated May 25, 2010, for European Application No. 05770170.8.
Office Action dated Oct. 24, 2010, in the Israel Patent Office for Israel Application No. 181261.
Office Action dated Feb. 25, 2010, in the Israel Patent Office for Israel Application No. 181261.
Translation of Second Office Action dated Sep. 27, 2010, in the State Intellectual Property Office of the People's Republic of China for Chinese Application No. 200580032474.1.
USPTO Office Action dated Apr. 27, 2010, in co-pending U.S. Appl. No. 11/463,659.
USPTO Office Action dated Oct. 27, 2010, in co-pending U.S. Appl. No. 11/463,659.
USPTO Office Action dated Apr. 22, 2010, in co-pending U.S. Appl. No. 10/599,963 (Now U.S. Patent No. 7,847,274).
USPTO Advisory Acton dated Jun. 22, 2010, in co-pending U.S. Appl. No. 10/599,963 (Now U.S. Patent No. 7,847,274).
USPTO Notice of Allowance dated Jul. 30, 2010, in co-pending U.S. Appl. No. 10/599,963 (Now U.S. Patent No. 7,847,274).
Amendment in Response to Restriction Requirement dated Nov. 16, 2009, from the U.S. Patent and Trademark Office in U.S. Appl. No. 11/635,441 to Krag et al. (9 pages).
USPTO Examiner Interview Summary in U.S. Appl. No. 11/635,441 with mail date Apr. 8, 2011 (4 pages total).
Communication Relating to the Results of the Partial International Search dated Aug. 10 2006, from the International Searching Authority in Application No. PCT/IB2006/052771 (7 pages).
Office Action dated Feb. 8, 2010, in the Instituto Mexicano de la Propriedad Industrial for Mexican Application No. MX/a/2007/001783 (6 pages, including summary translation).
USPTO Examiner Interview Summary in U.S. Appl. No. 11/463,659 with mail date Aug. 16, 2011 (2 pages total).
USPTO Final Office Action with mail date Nov. 4, 2011, in U.S. Appl. No. 11/463,659 (9 pages total).
USPTO Office Action with mail date May 2, 2011, in U.S. Appl. No. 12/917,052 (6 pages total).
USPTO Office Action with mail date Aug. 30, 2010, in U.S. Appl. No. 12/697,139 (9 pages total).
USPTO Examiner Interview Summary in U.S. Appl. No. 12/697,139 with mail date Nov. 17, 2010 (4 pages total).
USPTO Office Action with mail date Apr. 27, 2011, in U.S. Appl. No. 12/697,139 (9 pages total).

* cited by examiner

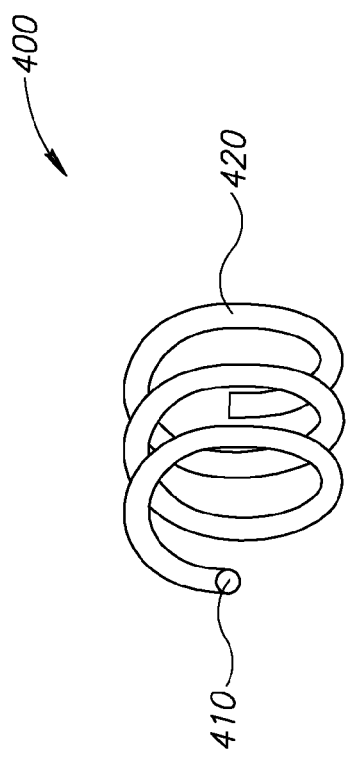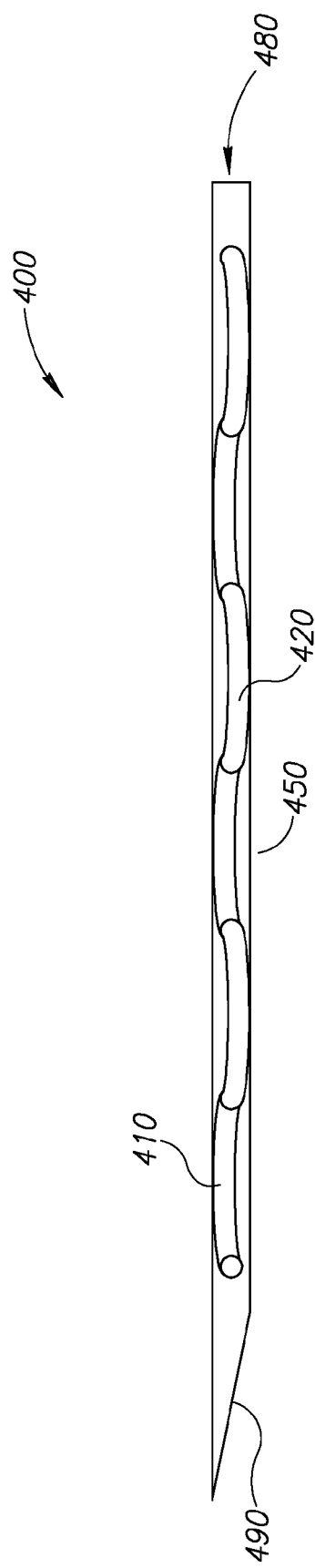
FIG4A
FIG4B

GUIDING A TOOL FOR MEDICAL TREATMENT BY DETECTING A SOURCE OF RADIOACTIVITY

RELATED APPLICATION DATA

This Application claims benefit under §119(e), directly or indirectly, from U.S. Provisional Applications:
60/773,931 filed on Feb. 16, 2006, entitled "Radiation Oncology Application";
60/804,178 filed on Jun. 8, 2006, entitled "Radioactive Medical Implants";
60/773,930 filed Feb. 16, 2006, entitled "Localization of a Radioactive Source";
The disclosures of these applications are fully incorporated herein by reference.
This application is a continuation-in-part of:
PCT/IL2005/000871 filed on Aug. 11, 2005, entitled "Localization of a Radioactive Source within a Body of a Subject"; and PCT/IL2005/001101 filed on Oct. 19, 2005; entitled "Tracking a Catheter Tip by Measuring its Distance From a Tracked Guide Wire Tip".
The disclosures of these applications are fully incorporated herein by reference.
This Application is related to:
U.S. Provisional Application 60/600,725 filed on Aug. 12, 2004, entitled "Medical Navigation System Based on Differential Sensor";
U.S. Provisional Application 60/619,792 filed on Oct. 19, 2004, entitled "Using a Catheter or Guidewire Tracking System to Provide Positional Feedback for an Automated Catheter or Guidewire Navigation System";
U.S. Provisional Application 60/619,897 filed on Oct. 19, 2004, entitled "Using a Radioactive Source as the Tracked Element of a Tracking System";
U.S. Provisional Application 60/619,898 filed on Oct. 19, 2004, entitled "Tracking a Catheter Tip by Measuring its Distance from a Tracked Guide Wire Tip";
International Patent Application, entitled "Localization of a Radioactive Source"; International Patent Application, entitled "Medical Treatment System and Method"; and US Patent Application, entitled "Medical Treatment System and Method", all filed on even date as this application.
The disclosures of these applications are fully incorporated herein by reference.

FIELD OF THE INVENTION

The present invention relates, in general, to guiding diagnostic and/or therapeutic procedures using a radioactivity based position sensor.

BACKGROUND OF THE INVENTION

In many medical procedures a target tissue is identified by medical imaging (e.g. computerized tomography or fluoroscopy). However, subsequent medical procedures (e.g. biopsy or excision) may be performed after the imaging procedure has been concluded. In some cases the target tissue is similar to surrounding non target tissue. In the case of a needle biopsy, an operative portion of the biopsy tool is hidden from medical personnel within the patient.

A particular type of guided procedure is radiation therapy. In conventional radiation therapy, ionizing radiation applied as a beam from a radiation source outside the body is used to kill a target tissue (e.g. tumor) in a particular region within the body. In regions of the body where the tissue moves relative to external landmarks it is difficult to provide accurate positional information in order to correctly aim the beam. As a result a larger region than the actual target is often irradiated to ensure that the region to be treated is actually subject to therapeutically cytotoxic doses of radiation. Collateral tissue damage often results. Efforts to reduce collateral tissue damage may result in under-treatment of the intended target.

Brachytherapy Seed Designs

To avoid collateral tissue damage, in brachytherapy, ionizing radiation is applied to a target by implantation of a brachytherapy "seed" which produces cytotoxic ionizing radiation, instead of radiation by a beam. The seed is implanted within the body in proximity to the target.

U.S. Pat. No. 6,436,026 to Sioshani (RadioMed Corp.) and US 2004/0116767 by Lebovic disclose spiral configuration brachytherapy seeds. The Lebovic application discloses delivery of the seed via a needle. The disclosures of these applications are fully incorporated herein by reference.

WO 02/078785 by Radiovascular Inc.; WO 2004/026111 by Microsperix LLC.; U.S. Pat. No. 6,749,555 to Winkler (Proxima Therapeutics inc.); US 2003/0158515 by Gonzalez (Spiration Inc.) each disclose brachytherapy seed designs which anchor themselves within the body. The disclosures of these applications and patents are fully incorporated herein by reference.

Conventional Radiation Therapy: Aiming Systems

U.S. Pat. No. 4,215,694 to Isakov teaches a device for tracking the position of an irradiated object and an electromechanical drive unit for aiming a beam source. The device for tracking the position relies upon sensors in the form of pulse transformers. The disclosure of this patent is fully incorporated herein by reference.

WO0154765 by ZMED teaches a system for aiming a radiation beam by aligning a frame (bed) holding a patient. The disclosure of this application is fully incorporated herein by reference.

WO 97/29699 and WO 97/29700 both disclose use of an intrabody probe to monitor applied radiation from an external source at/near a target and adjust the amount of applied radiation in response to the monitoring. The disclosures of these applications are fully incorporated herein by reference.

Implantable Markers for Position Determination

US 2005/0261570 by Mate teaches implantation of excitable markers in/near a target. An external excitation source is then aimed at the marker to excite it. The excitation energy is used for position determination. Therapeutic radiation is aimed at a position determined by the target excitation energy. The disclosure of this application is fully incorporated herein by reference.

US 2005/0027196 by Fitzgerald teaches a system for processing patient radiation treatment data. Fitzgerald teaches use of imaging equipment to determine positions of brachytherapy radiation sources implanted in a patient. The disclosure of this application is fully incorporated herein by reference.

WO 00/57923 teaches a radioactive seed which discloses the orientation and location of the seed when exposed to X-ray. Orientation is indicated by use of different radio-opaque materials. The disclosure of this application is fully incorporated herein by reference.

US 2005/0197564 by Dempsey teaches use of MRI to identify where tracer is taken up, as ionizing radiation is applied. The disclosure of this application is fully incorporated herein by reference.

A series of US patents assigned to Calypso Medical Technologies (e.g. U.S. Pat. Nos. 6,977,504; 6,889,833; 6,838,990; 6,822,570 and 6,812,842) describe use of AC electromagnetic localization transponders in conjunction with a position determination system. The disclosures of these patents are fully incorporated herein by reference.

Location Determination by Monitoring Intrabody Radiation

Co-pending application PCT/IL2005/000871 by the inventors of the present invention and U.S. Pat. No. 6,603,124 to Maublant teach the use of directional sensors for detecting a direction towards a gamma emitting source and aiming the sensor towards the source. The disclosures of this application and this patent are fully incorporated herein by reference.

SUMMARY OF THE INVENTION

An aspect of some embodiments of the invention relates to use of an intrabody radiation source to aim an external tool at an intrabody target. In an exemplary embodiment of the invention, the external device is a biopsy tool and/or ablation tool and/or excision tool and the target is a tumor or other lesion. In an exemplary embodiment of the invention, the external device is a cytotoxic beam and the target is a tumor. In an exemplary embodiment of the invention, the external device is a light beam and the target is an area of skin indicating a recommended access route for a surgeon performing a tumor excision. Optionally, the light beam is a laser beam. Alternatively or additionally, the light beam is a patterned beam, optionally projected, optionally collimated and/or focused.

In some embodiments of the invention the tool is designed for use outside the body or with open surgical wounds, for example a scalpel. In other embodiments, the tool is a guided tool, optionally a flexible tool, for example as used in laparoscopy or endoscopy. In an exemplary embodiment of the invention, a radioactive marker is used to guide the tool to the target. Optionally, the tool is fitted with a radioactive marker, so that a position sensor can determine the relative locations of the two markers. Alternatively or additionally, the tool is optionally mechanically coupled to a sensor or has its position relative to the sensor measured using other means (such as other position sensing modalities, such as known in the art, for example, light based, electromagnetic, magnetic or ultrasonic).

In an exemplary embodiment of the invention, the external tool and sensors which determine a position of the intrabody radiation source are each independently positionable with respect to the intrabody target. Alternatively or additionally, one or both are registered to the patient's body, for example, mechanically or using a different position sensing method.

In an exemplary embodiment of the invention, the radiation source is used to generate only a relative location, rather than an absolute location, in some embodiments, the relative location comprises a direction of motion, in one, two or three axes which will align the tool with and/or position the tool at the target or at a desired location near the target.

In an exemplary embodiment of the invention, the implanted (or body surface) marker is used to help select an anatomical image for display. Optionally, the marker is injected to the body prior to acquisition of the anatomical image or a correlated image and the marker is designed for imaging by the imaging modality used (e.g., radio-opaque for x-ray CT). Optionally, the current location and/or expected path of a tool is shown on the image, for example as an overlay. Optionally, an expert system or other software is used to select a path for the tool which does not interfere with the system (e.g., the position sensor and/or a frame thereof) and/or important body structures. Optionally, the positioning volume and/or expected accuracy of positioning is indicated on the display.

In an exemplary embodiment of the invention, the intrabody target is in motion. Optionally, the external device is a cytotoxic beam which tracks a moving target. Optionally, the beam is aimed at the moving target by adjusting a position and/or angle of the cytotoxic beam. Optionally, the beam is aimed at the moving target by adjusting a position of an examination table/bed to keep the target in the beam as the target moves along the trajectory. In an exemplary embodiment of the invention, the beam and the bed are both adjusted to keep the beam aimed at the moving target.

In an exemplary embodiment of the invention, the intrabody radiation source includes an implantable position indicator comprising a low activity radiation source. In an exemplary embodiment of the invention, the implantable position indicator includes a fixation element. Low activity encompasses any radiation source which does not cause a clinically significant degree of cytotoxicity during a period of seven days. In an exemplary embodiment of the invention, the radiation source has an activity of 10 µCi or less.

In an exemplary embodiment of the invention, the radiation source has at least one dimension less than 3 mm, optionally less than 2 mm, optionally 1 mm, optionally 0.5 mm or lesser or intermediate values. Optionally, the radioactive source is supplied as an approximately spherical solid object with a diameter of approximately 0.5 mm or less. Optionally, the radioactive source is supplied as an approximately spherical adhesive drop with a diameter of approximately 3.0 mm or less.

In an exemplary embodiment of the invention, the position indicator includes a fixation element integrally formed with or attached to the source. Optionally, the fixation element is adapted to prevent migration and/or unwanted dispersal of the source within the body. Optionally, the fixation element employs a physical configuration and/or an adhesive material and/or a coating to make the source self anchoring.

Optionally, the position indicator includes a radio-opaque portion. In an exemplary embodiment of the invention, the radio-opaque portion allows visualization of the position indicator using X-ray based imaging methods. Optionally, visualization is useful during placement of the position indicator near a target.

In an exemplary embodiment of the invention, the intrabody radiation source is supplied as a kit including an implantable position indicator as described above together with an implantation needle adapted to contain the position indicator and an ejection tool adapted to expel the position indicator from the injection needle. In an exemplary embodiment of the invention, the position indicator is inserted into the implantation needle at a manufacturing facility. Optionally, the ejection tool is inserted into the implantation needle at a manufacturing facility.

An aspect of some embodiments of the present invention relates to a position determination system configured to determine a position of an intrabody radiation source of the type described above with sufficient accuracy to aim a therapeutic device at a target (e.g. tumor). Optionally, the therapeutic device includes a cytotoxic beam and/or ablation tool and/or biopsy tool. In exemplary embodiments of the invention which include a therapeutic beam, position determination optionally occurs whether the beam is operative or inoperative. In an exemplary embodiment of the invention, the system aims a cytotoxic beam at a tumor.

In an exemplary embodiment of the invention, aiming includes moving the target and/or subjecting the tool to linear displacement and/or angular displacement.

In an exemplary embodiment of the invention, position determination system determines a series of temporally defined positions of the position indicator as a trajectory, optionally a cyclically repeating trajectory. Optionally, the therapeutic device is aimed at one or more points calculated based on the trajectory at a time when the target is expected to be there.

In an exemplary embodiment of the invention, the system relies upon one or more directional sensors to determine the position of the intrabody radiation source. The position sensors optionally include collimators, which are optionally ring collimators. Optionally the beam or tool is aimed at the determined position or at a target with a defined spatial relationship with respect to the determined position. The term "aiming" as used herein optionally refers to moving a target into a beam path or tool path (or vice-versa) or optionally refers to providing information to a user that enables the user to move the target, beam and/or tool such that the target lies in the tool/beam path.

In an exemplary embodiment of the invention, the directional sensors are positioned so as not to interfere with a therapeutic beam when the beam is operational. Interference may be in the form of, for example, scatter, reflection, or absorption. Optionally, the directional sensors are positioned in a first location while they are operative and are moved to a second location when the beam is operative. In an exemplary embodiment of the invention, the therapeutic beam is delivered in pulses and the sensors return to the first location after each pulse and move back to the second location prior to a subsequent pulse. Optionally, position determination by the sensors occurs between pulses.

In an exemplary embodiment of the invention, the directional sensors are gated so that they do not operate while the beam is operative.

In an exemplary embodiment of the invention, the directional sensors are placed so that an amount of radiation from the beam which impinges upon them is reduced.

In some exemplary embodiments of the invention, the system provides the position as an output to a radiotherapy system which aims the beam. Optionally, the output is manually entered into the radiotherapy system after being displayed to an operator of the radiotherapy system. Optionally, the manually entered output may cause the radiotherapy system to aim a therapeutic beam source and/or reposition a patient so that a target is in line with the beam. In an exemplary embodiment of the invention, patient repositioning is accomplished by moving a bed and/or therapy table.

In some exemplary embodiments of the invention, the position determination system is integrated into a radiotherapy system which aims the beam.

An aspect of some embodiments of the invention relates to use of an injected volume of a bioadhesive glue as a brachytherapy seed or as a carrier for a seed. Optionally, the glue contains a radio-opaque marker in addition to a radioactive isotope. In an exemplary embodiment of the invention, use of a bioadhesive glue reduces seed migration.

For purposes of this specification and the accompanying claims, the term "position" refers to a set of co-ordinates. Optionally, the co-ordinates are 2D or 3D co-ordinates. Optionally, the co-ordinates are temporally, as well as spatially defined. In some embodiments, the methods use locations, for example relative locations or direction. It is noted that the position/location/direction may intentionally allow a freedom in the other axes. It is also noted that in some embodiments, for example, aiming a tool or a beam, the orientation of the aimed item may also be determined. Optionally, an orientation of a body is generated using more than one implanted markers and solving equations that convert marker positions into a plane the markers lie in and relative to which a tool and/or beam may be oriented.

In an exemplary embodiment of the invention, sensors determine a position within 5, 4, 3, 2 or 1 seconds.

In an exemplary embodiment of the invention, the position is determined with an accuracy of 5, 4, 3, 2 or 1 mm.

There is provided an implantable position indicator; the position indicator comprising:
(a) a radioactive source characterized by an activity which does not cause clinically significant cytotoxicity in a period of seven days; and
(b) a fixation element integrally formed with or attached to said source, the fixation element adapted to prevent migration of the source within the body.

Optionally, the fixation element additionally prevents dispersal of the source within the body Optionally, the activity is less than 100 µCi.
Optionally, the activity is less than 50 µCi.
Optionally, the activity is less than 25 µCi.
Optionally, the activity does not exceed 10 µCi.
Optionally, the fixation element includes a solid substrate.
Optionally, at least a portion of the solid substrate is characterized by a curved configuration, the curved configuration characterized by an elastic memory.
Optionally, the curved configuration includes at least a portion of a spiral or helix.
Optionally, the position indicator includes at least one filament characterized by an elastic memory.
Optionally, the solid substrate is at least partially coated with a bioadhesive material.
Optionally, the fixation element includes an adhesive material.
Optionally, the fixation element functions as a biocompatible coating.
Optionally, the position indicator includes a radio-opaque portion.

In an exemplary embodiment of the invention, there is provided a method of aiming a therapeutic beam, the method comprising:
(a) implanting a source of radioactive emissions, optionally characterized by an activity which does not cause clinically significant cytotoxicity in a period of 7 days in a patient at a geometric relationship to a target tissue. Optionally, the source is attached to, or integrally formed with, a fixation element and has a biocompatible outer surface;
(b) employing at least one position sensor to determine a position of said source based upon the radioactive emissions; and
(c) employing said position and said relationship to align a therapeutic beam and said target with one another.

Optionally, the source is characterized by an activity which does not cause clinically significant cytotoxicity in a period of 7 days.

Optionally, the method includes determining said geometric relationship between said target and said source.

Optionally, the position sensor employs at least one radiation shield.

Optionally, the position sensor employs a collimator.

Optionally, the method includes registration of a first position co-ordinate system employed by said sensor and a second position co-ordinate system employed by a beam aiming mechanism with respect to one another.

Optionally, the method includes:
(d) irradiating said target with a therapeutic dose of radiation emanating from said beam.

Optionally, the method includes alternating between (b) and (d).

Optionally, the method includes deploying said position sensor so that an amount of radiation originating from said beam and impinging on said sensor does not significantly affect an ability of said sensor to determine a position of said source.

Optionally, the method includes configuring said position sensor with an energy window which substantially excludes radiation originating from said beam and includes a significant portion of radiation emanating from said source.

Optionally, (c) includes moving said target to a desired position.

Optionally, (c) includes moving said therapeutic beam to a desired position.

Optionally, (c) includes subjecting said therapeutic beam to an angular adjustment.

In an exemplary embodiment of the invention, there is provided a therapy system, the system comprising;
(a) a source of radioactive emissions optionally characterized by an activity which does not cause clinically significant cytotoxicity in seven days, alternatively or additionally, the source optionally attached to, or integrally formed with, a fixation element and having a biocompatible outer surface. The source is optionally implanted in a patient at a fixed geometric relationship to a target;
(b) a position sensing module capable of determining a position of said source based upon the radioactive emissions and providing a position output signal, responsive to the determination;
(c) control circuitry configured to receive the position output signal, calculate a target location based upon the position output signal and the geometric relationship and provide target coordinates to a beam-target alignment mechanism;
(d) a beam source; and
(e) a beam-target alignment mechanism configured to align said beam source and said target according to said target coordinates.

Optionally, the activity is in the range of 1 µCi to 100 µCi.

Optionally, the position sensing module employs at least one position sensor which employs at least one radiation shield.

Optionally, the position sensor employs a collimator.

Optionally, the therapy system includes:
(f) circuitry adapted for registration of a first position co-ordinate system employed by said sensor module and a second position co-ordinate system employed by a beam aiming mechanism with respect to one another.

Optionally, the therapy system alternates between operation of (b) and (d).

Optionally, the therapy system is configured to ignore output from and/or disable position sensing module of (b) while (d) is in operation.

Optionally, the position sensor is positioned so that an amount of radiation originating from said beam and impinging on said sensor does not significantly affect an ability of said sensor to determine a position of said source.

Optionally, the position sensor is configured with an energy window which substantially excludes radiation originating from said beam and includes a significant portion of radiation emanating from said source.

Optionally, the beam-target alignment mechanism is configured to move said target to a desired position in response to said target co-ordinates.

Optionally, the beam-target alignment mechanism is configured to move said therapeutic beam to a desired position.

Optionally, the beam-target alignment mechanism is configured to subject said therapeutic beam to an angular adjustment.

In an exemplary embodiment of the invention, there is provided an implantation kit, the kit comprising:
(a) a radioactive source having a biocompatible outer surface, the source characterized by an activity which does not cause clinically significant cytotoxicity and coupled to or integrally formed with a fixation element;
(b) an injection needle containing the source; and
(c) an ejection mechanism adapted to eject said source from said needle into a subject.

Optionally, the activity is in the range of 1 µCi to 100 µCi.

Optionally, the activity does not exceed 10 µCi.

Optionally, the fixation element includes a solid substrate.

Optionally, at least a portion of the solid substrate is characterized by a curved configuration, the curved configuration characterized by an elastic memory.

Optionally, the curved configuration includes at least a portion of a spiral or helix.

Optionally, the source includes at least one filament characterized by an elastic memory.

Optionally, the solid substrate is at least partially coated with a bioadhesive material.

Optionally, the fixation element includes an adhesive material.

Optionally, the fixation element functions as a biocompatible coating.

Optionally, the source includes a radio-opaque portion.

In an exemplary embodiment of the invention, there is provided a method of aiming an external device, the method comprising:
(a) implanting a source of radioactive disintegrations optionally characterized by an activity which does not cause clinically significant cytotoxicity, the source being implanted in a subject at a fixed geometric relationship to a target. Optionally, the source being attached to, or integrally formed with, a fixation element and having a biocompatible outer surface;
(b) determining said fixed geometric relationship between said target and said source;
(c) employing at least one position sensor to determine a position of said source based upon the radioactive disintegrations; and
(d) employing said position and said relationship to align an external tool and said target with one another.

Optionally, the external tool includes a therapeutic beam.

Optionally, the external tool includes a light beam.

Optionally, the external tool includes an excision tool.

In an exemplary embodiment of the invention, there is provided a therapy system, the system comprising;
(a) a source of radioactive disintegrations optionally characterized by an activity which does not cause clinically significant cytotoxicity. Optionally, the source being attached to, or integrally formed with, a fixation element and/or having a biocompatible outer surface. The source being implanted in a subject at a fixed geometric relationship to a target;
(b) a tool;

(c) a position sensing module capable of determining a position of said source based upon the radioactive disintegrations and providing the position as a position output signal;
(d) control circuitry configured to receive the position output signal, calculate a target location based upon the position output signal and the geometric relationship and provide target coordinates to a tool-target alignment mechanism; and
(e) the tool-target alignment mechanism configured to align said tool and said target according to said target coordinates.

Optionally, the tool includes a therapeutic beam.
Optionally, the tool includes a light beam.
Optionally, the tool includes an excision tool.

In an exemplary embodiment of the invention, there is provided a radiation source, the source consisting essentially of:
(a) at least one radioactive isotope; and
(b) a quantity of biocompatible adhesive containing said isotope.

There is also provided in accordance with an exemplary embodiment of the invention, a method of aiming a therapeutic beam, the method comprising:
(a) implanting a source of radioactive emissions in a patient at a position having a geometric relationship to a target tissue;
(b) determining at least an indication of a location of said source using at least one radioactivity detecting position sensor; and
(c) automatically aiming a therapeutic beam at said target based on said at least an indication of location.

In an exemplary embodiment of the invention, said geometric relationship is known prior to said implanting.

In an exemplary embodiment of the invention, said geometric relationship is determined after said implanting using imaging.

In an exemplary embodiment of the invention, automatically aiming comprises maintaining said aim while at least one of said target and said beam move.

In an exemplary embodiment of the invention, said determined location is a location relative to said sensor.

In an exemplary embodiment of the invention, determining at least an indication of a location comprises determining a direction.

In an exemplary embodiment of the invention, said position sensor generates a direction signal.

In an exemplary embodiment of the invention, the location is determined in three dimensions.

In an exemplary embodiment of the invention, the source is characterized by an activity which does not cause clinically significant cytotoxicity in a period of 7 days.

In an exemplary embodiment of the invention, the source is attached to, or integrally formed with, a tissue fixation element adapted to maintain said source in said geometrical relationship.

In an exemplary embodiment of the invention, the source includes a biocompatible outer surface.

In an exemplary embodiment of the invention, the source location is determined with an error not exceeding 2 mm.

In an exemplary embodiment of the invention, the source location is determined with an error not exceeding 1 mm.

In an exemplary embodiment of the invention, determining at least an indication of a location comprises determining a series of location indications as affected by a physiological motion cycle. Optionally, said cycle comprises breathing.

In an exemplary embodiment of the invention, determining at least an indication of a location comprises providing a series of temporally defined locations which define a trajectory.

In an exemplary embodiment of the invention, the method comprises registering a first position co-ordinate system employed by said sensor and a second position co-ordinate system employed by a beam aiming mechanism with respect to one another.

In an exemplary embodiment of the invention, the method comprises:
(d) irradiating said target with a therapeutic dose of radiation using said beam. Optionally, the method comprises alternating between (c) and (d). Alternatively or additionally, the method comprises positioning at least one of said position sensor and said beam so that an amount of radiation originating from said beam and impinging on said sensor does not significantly affect an ability of said sensor to determine a location of said source.

In an exemplary embodiment of the invention, (c) includes moving said target to a desired location.

In an exemplary embodiment of the invention, (c) includes moving said therapeutic beam to a desired position.

In an exemplary embodiment of the invention, (c) includes subjecting said therapeutic beam to an angular adjustment.

In an exemplary embodiment of the invention, the method comprises supporting said patient using a frame mechanically coupled to said at least one radioactivity detecting position sensor.

In an exemplary embodiment of the invention, (c) comprises at least one of aiming said beam to miss said sensor and moving said sensor to be out of a path of said beam. Optionally, the method comprises predetermining a motion of the at least one position sensor to avoid irradiation by said beam. Optionally, the method comprises selecting a location for said at least one sensor, taking into account a desired therapy of said target, said location designed to avoid said beam. Alternatively or additionally, the method comprises using an angle of a patient couch adapted for receiving said patient and an angle of said beam to determine an expected interaction between said beam and said at least one sensor.

There is also provided in accordance with an exemplary embodiment of the invention, a therapy system, the system comprising:
(a) a position sensing module capable of determining at least an indication of a location of an implantable radioactive source based upon radioactive emissions of said source and providing a position output signal, responsive to the determination;
(b) control circuitry configured to receive the position output signal, calculate an alignment correction based on said signal and provide said correction to a beam-target alignment mechanism;
(c) a beam source; and
(d) a beam-target alignment mechanism configured to align said beam source and said target according to said correction. Optionally, the target location is defined in three dimensions. Alternatively or additionally, said alignment mechanism is configured to align based on a desired therapeutic effect. Alternatively or additionally, said alignment mechanism is configured to align based on a desired safety effect. Alternatively or additionally, said alignment mechanism is configured to align based on a desired lack of interaction between said module and said beam. Alternatively or additionally, the sensing module is capable of determining a location indication in less than 1 second and an accuracy of better than 5 mm, for a source characterized by an activity which does not cause clinically significant cytotoxicity in a period of 7 days. Optionally, the activity is in the range of 1 µCi to 300 µCi. Optionally, the activity is in the range of 1 µCi to 100 µCi.

In an exemplary embodiment of the invention, the position sensing module employs at least one position sensor which employs at least one radiation shield. Optionally, the position sensor employs a collimator.

In an exemplary embodiment of the invention, the position sensor employs a differential radiation detector.

In an exemplary embodiment of the invention, the position sensor employs a rotating radiation sensor with angular sensitivity.

In an exemplary embodiment of the invention, the target location is calculated with an error not exceeding 2 mm.

In an exemplary embodiment of the invention, the target location is calculated with an error not exceeding 1 mm.

In an exemplary embodiment of the invention, said control circuitry is configured for registering a first position co-ordinate system employed by said sensor module and a second position co-ordinate system employed by a beam aiming mechanism with respect to one another.

In an exemplary embodiment of the invention, the system is configured to alternate between position sensing and patient irradiation.

In an exemplary embodiment of the invention, the system is configured to ignore a position output signal generated while said beam is in operation.

In an exemplary embodiment of the invention, the system is configured to inactivate said position sensing module while said beam is in operation.

In an exemplary embodiment of the invention, said position sensing module is positioned so that an amount of radiation originating from said beam and impinging on said position sensing module does not significantly affect an ability of said position sensing module to determine a position of said source.

In an exemplary embodiment of the invention, said beam-target alignment mechanism is configured to move said target to a desired position in response to said target co-ordinates.

In an exemplary embodiment of the invention, said beam-target alignment mechanism is configured to move said therapeutic beam to a desired position.

In an exemplary embodiment of the invention, said beam-target alignment mechanism is configured to subject said therapeutic beam to an angular adjustment.

In an exemplary embodiment of the invention, the control circuitry is adapted to provide the correction as a series of temporally defined sets of co-ordinates which define a trajectory.

In an exemplary embodiment of the invention, a position sensor of the position sensing module is provided within a patient support adapted to hold a patient during therapy.

In an exemplary embodiment of the invention, the system includes at least one radiation shield adapted to be shield said sensor from radiation, by movement of at least one of said sensor and said shield. Alternatively or additionally, said patient support is rotatable.

In an exemplary embodiment of the invention, said sensing module is adapted to move within said support.

In an exemplary embodiment of the invention, the system includes a sensor displacement mechanism adapted to position at least one sensor of the position sensing module outside of a beam path when the beam source is operative.

There is also provided in accordance with an exemplary embodiment of the invention, a method of aiming a therapeutic beam, the method comprising:

(a) implanting a source of radioactive emissions in a patient at a position having a geometric relationship to a target tissue;
(b) detecting said source using at least one radioactivity detecting position sensor; and
(c) automatically aiming a therapeutic beam at said target based on detecting.

There is also provided in accordance with an exemplary embodiment of the invention, a therapy control system, the system comprising:

(a) a position sensing module configured to determine at least an indication of a location of an implantable radioactive source based upon radioactive emissions of said source and providing a position output signal, responsive to the determination; and
(b) control circuitry configured to receive the position output signal and calculate and output at least one of target coordinates and tool aiming instructions to an output channel, based upon the position output signal.

There is also provide din accordance with an exemplary embodiment of the invention, a method of guiding a tool, the method comprising:

(a) implanting a source of radioactivity at a position having a geometric relationship to a target tissue;
(b) determining at least an indication of a location of said source using at least one radioactivity detecting position sensor; and
(c) positioning a tool at a desired relative location with respect to said target tissue based on said determined location.

Optionally, said geometric relationship is known prior to said implanting.

In an exemplary embodiment of the invention, said geometric relationship is determined after said implanting using imaging.

In an exemplary embodiment of the invention, the method comprises:

(d) causing at least a portion of said tool to enter the patient and approach said target tissue.

In an exemplary embodiment of the invention, positioning comprises maintaining said relative location while at least one of said target and said tool move.

In an exemplary embodiment of the invention, determining at least an indication of a location comprises determining a direction.

In an exemplary embodiment of the invention, said position sensor generates a direction signal.

In an exemplary embodiment of the invention, the positioning includes positioning directed by a positioning mechanism.

In an exemplary embodiment of the invention, the positioning includes manual positioning.

In an exemplary embodiment of the invention, the method comprises tracking a position of said tool. Optionally, said tracking utilizes a non-ionizing position sensing method.

In an exemplary embodiment of the invention, the method comprises determining an orientation of said tool.

In an exemplary embodiment of the invention, the method comprises determining a relative position of said tool and said sensor.

In an exemplary embodiment of the invention, the location is defined in three dimensions.

In an exemplary embodiment of the invention, the location is defined as a relative location with respect to the target tissue.

In an exemplary embodiment of the invention, the source is characterized by an activity which does not cause clinically significant cytotoxicity in a period of 7 days.

In an exemplary embodiment of the invention, the source is attached to, or integrally formed with, a fixation element.

In an exemplary embodiment of the invention, the source includes a biocompatible outer surface adapted to maintain said source in said geometrical relationship.

In an exemplary embodiment of the invention, the source location is calculated with an error not exceeding 2 mm.

In an exemplary embodiment of the invention, the source location is calculated with an error not exceeding 1 mm.

In an exemplary embodiment of the invention, determining at least an indication of a location comprises determining a series of indications of locations as affected by a physiological motion cycle. Optionally, said cycle comprises breathing.

In an exemplary embodiment of the invention, causing at least a portion of said tool to enter the patient is timed with respect to the physiological motion cycle.

In an exemplary embodiment of the invention, determining an indication of a location comprises providing a series of temporally defined locations which define a trajectory.

In an exemplary embodiment of the invention, the method comprises registering of a first position co-ordinate system employed by said sensor and a second position co-ordinate system employed by the tool with respect to one another.

In an exemplary embodiment of the invention, the method comprises:
(e) removing at least a portion of said target tissue with said tool.

In an exemplary embodiment of the invention, the method comprises:
(e) delivering a therapeutic agent to said target tissue with said tool.

In an exemplary embodiment of the invention, the method comprises repositioning the tool at least one time and removing at least one additional portion of said target tissue.

In an exemplary embodiment of the invention, the positioning includes moving said tool to a desired position.

In an exemplary embodiment of the invention, the positioning includes subjecting said tool to an angular adjustment.

In an exemplary embodiment of the invention, the method comprises supporting said patient by a frame mechanically coupled to said at least one radioactivity detecting position sensor.

In an exemplary embodiment of the invention, the method comprises attaching a tool control unit to a frame mechanically coupled to said position sensor.

In an exemplary embodiment of the invention, the method comprises providing the at least one position sensor within a piece of furniture adapted to hold a patient during therapy.

In an exemplary embodiment of the invention, said tool includes a light beam.

There is also provided in accordance with an exemplary embodiment of the invention, a therapy system, the system comprising;
(a) a position sensing module capable of determining a position of an implantable radioactive source based upon radioactive emissions of said source and providing a position output signal, responsive to the determination;
(b) control circuitry configured to receive the position output signal, calculate a target location based upon the position output signal and provide at least an indication of target coordinates to an output; and
(c) an output adapted to receive said indication of target coordinates and adapted to assist in positioning a tool towards said target. Optionally, said output comprises:
(d) a tool positioning mechanism configured to position said tool with respect to said target according to said target output signal. Alternatively or additionally, said output comprises a visual display. Alternatively or additionally, the target co-ordinates are defined in three dimensions. Alternatively or additionally, said control circuitry is configured to generate said coordinates based on a desired therapeutic procedure. Optionally, said control circuitry is configured to generate said coordinates based on a desired safety effect.

In an exemplary embodiment of the invention, the sensing module is capable of determining a position in less than 1 second and an accuracy of better than 5 mm, for a source characterized by an activity which does not cause clinically significant cytotoxicity in a period of 7 days. Optionally, the activity is in the range of 1 µCi to 300 µCi. Optionally, the activity is in the range of 1 µCi to 100 µCi.

In an exemplary embodiment of the invention, the position sensing module employs at least one position sensor which employs at least one radiation shield. Optionally, the position sensor employs a collimator.

In an exemplary embodiment of the invention, the position sensor employs a differential radiation detector.

In an exemplary embodiment of the invention, the position sensor employs a rotating radiation sensor with angular sensitivity.

In an exemplary embodiment of the invention, the target coordinates are provided with an error not exceeding 2 mm.

In an exemplary embodiment of the invention, the target coordinates are provided with an error not exceeding 1 mm.

In an exemplary embodiment of the invention, said control circuitry is configured for registering a first position co-ordinate system employed by said sensor module and a second position co-ordinate system employed by the tool-target alignment mechanism with respect to one another.

In an exemplary embodiment of the invention, said tool alignment mechanism is configured to move said tool to a desired position.

In an exemplary embodiment of the invention, said tool alignment mechanism is configured to subject said tool to an angular adjustment.

In an exemplary embodiment of the invention, the target output signal comprises a series of temporally defined sets of co-ordinates which define a trajectory.

In an exemplary embodiment of the invention, the position sensing module comprises at least one position sensor installed within a patient support adapted to hold a patient during therapy. Optionally, at least a portion of said sensing module is positionable within said support. Optionally, at least one sensor of said sensing module is adapted to move independently of at least one additional sensor of said sensing module.

BRIEF DESCRIPTION OF DRAWINGS

In the FIGS, identical structures, elements or parts that appear in more than one FIGS are generally labeled with the same numeral in all the FIGS in which they appear. Dimensions of components and features shown in the FIGS are chosen for convenience and clarity of presentation and are not necessarily shown to scale. The FIGS are listed below.

FIGS. 4A and 4C are schematic representations of position indicators according to exemplary embodiments of the invention;

FIGS. 4B and 4D are schematic representations of the position indicators according to exemplary embodiments of the invention depicted in FIGS. 4A and 4C respectively loaded in an injection needle;

DETAILED DESCRIPTION OF EMBODIMENTS

Overview

Figure 1A:
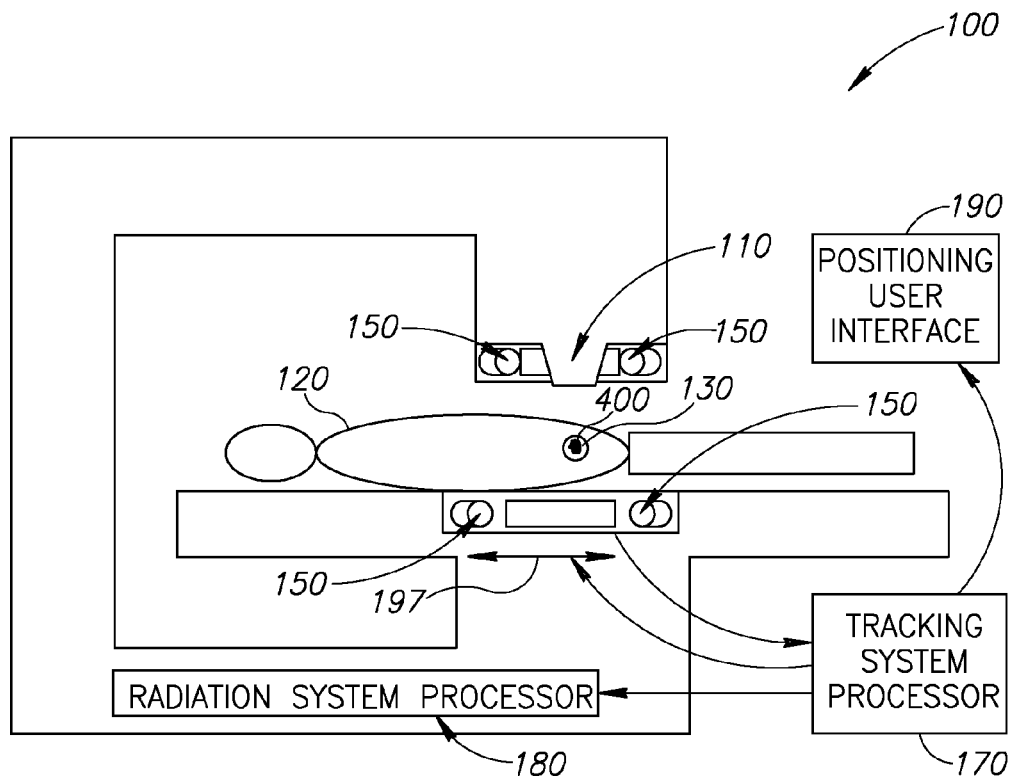
FIGS. 1A, 1B, 1C and 1D are schematic representations of radiation therapy systems according to exemplary embodiments of the invention.
Figure 1B:
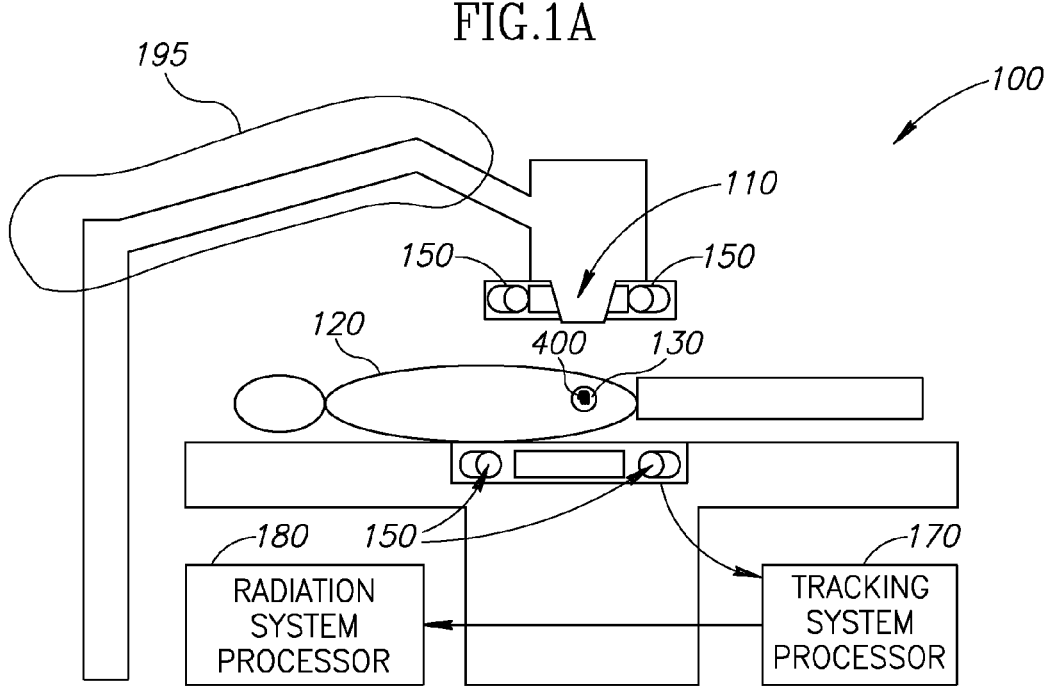

FIGS. 1A and 1B are schematic representations of exemplary radiation therapy systems 100 which rely upon radioactive disintegrations produced by an intrabody radiation source which can be in the form of a position indicator 400 located within a body of a patient 120. Position indicator 400 is optionally within, adjacent to or at a known geometric relationship with respect to a target tissue 130. Optionally, target tissue 130 is a tumor. Optionally, the implantation position and geometric relationship are selected ahead of time. Alternatively or additionally, the relationship may be determined after implanting, for example, by manual or automatic analysis of x-ray or CT images of the patient. Optionally, more than one marker is implanted, for example to assist in determining patient orientation.

In an exemplary embodiment of the invention, source 400 broadcasts its location radially outward as photons resulting from radioactive disintegrations. Optionally, a portion of this broadcast is received by one or more directional sensors 150 deployed for that purpose. Exemplary sensors 150 are described in co-pending application PCT/IL2005/000871 filed on Aug. 11, 2005, the disclosure of which is incorporated herein by reference. A summary of that description appears hereinbelow with reference to FIG. 5.

In an exemplary embodiment of the invention, sensors 150 employ collimators, optionally ring collimators, to determine a direction from which photons resulting from radioactive disintegrations originate. Optionally, each direction is expressed as a plane or as a linear vector. Optionally, two sensors 150 including ring collimators indicate a pair of lines which cross at a single point corresponding to a position of position indicator 400. In an exemplary embodiment of the invention, three or more sensors 150 are employed to increase the accuracy of a determined location. In an exemplary embodiment of the invention, three or more sensors 150 including collimators, optionally slat collimators, indicate planes which cross at a single point corresponding to a position of position indicator 400.

FIG. 1A illustrates an exemplary semiautomatic system 100 for aiming a therapeutic radiation beam 110. In an exemplary embodiment of the invention, beam 110 is configured to deliver a cytotoxic dose of radiation to a target, for example a tumor. In additional exemplary embodiments of the invention, beam 110 is generally indicative of any external tool which is aimable. Optionally, such external aimable tools include, but are not limited to biopsy tools (e.g. needles), ablation tools (e.g. electrodes or ultrasonic probes) and laser beams.

According to the pictured exemplary system, sensors 150 adjust their direction to optimize reception of the incident particles resulting from radioactive disintegrations. Once reception is optimized, each sensor indicates a direction to tracking system processor 170. Processor 170 calculates a position from the direction input supplied by all of sensors 150. Optionally, processor 170 corrects for a known spatial displacement between position indicator 400 and target tissue 130. Optionally, the nearest point of approach of the two, optionally three or more, lines, or three, optionally four or more, planes, is deemed to be the point at which the lines or planes cross.

As indicated in FIG. 1, sensors 150 may optionally be deployed above patient 120 (e.g. around beam source 110 as in FIG. 1A) and/or below patient 120 (e.g. built into the examination table as in FIGS. 1B, 1C and 1D).

In an exemplary embodiment of the invention, positioning sensors 150 around beam source 110 as depicted in FIG. 1A prevents scatter and/or reflection, and/or absorption of a therapeutic beam by ensuring that sensors 150 are not in a path of the beam.

In other exemplary embodiments of the invention, positioning sensors 150 below the patient as depicted in FIG. 1B can make scatter and/or reflection, and/or absorption of a therapeutic beam a potential problem if sensors 150 are in a path of the beam. A solution to this potential problem is provided by exemplary embodiments depicted in FIGS. 1C and 1D which are described hereinbelow.

In the exemplary semi-automatic system shown, processor 170 supplies a position output signal to positioning user interface 190. An operator of the system then supplies the position to radiation system processor 180 which responds by adjusting platform translation mechanism 197 so that radiation beam source 110 is aimed at target 130. An exemplary semi-automatic system of this type may be useful, for example, in a retrofit situation in which system 100 was not originally designed to employ a position indicator 400.

FIG. 1A also illustrates exemplary fully automatic embodiments in which tracking system processor 170 communicates the position output signal directly to radiation system processor 180 and/or translation mechanism 197 installed in the examination table. According to this exemplary embodiment of the invention radiation beam source 110 is aimed at target 130 without additional operator input.

FIG. 1B depicts additional exemplary embodiments of the invention in the context of a radiosurgery system in which the beam source 110 (e.g. a LINAC) is mounted on a robotic arm 195 (e.g. CyberKnife Accuray; Sunnyvale; CA, USA), mounted on a base 116 (e.g., attached to a ceiling, a wall, a frame and/or a floor). As described above, sensors 150 are mounted either in the examination table or adjacent to LINAC 110. In this exemplary system 100, processor 170 communicates the position output signal directly to radiation system processor 180 and/or robotic arms 195 supporting beam source 110. According to this exemplary embodiment of the invention radiation beam source 110 is aimed at target 130 without additional operator input.

Figure 1C:
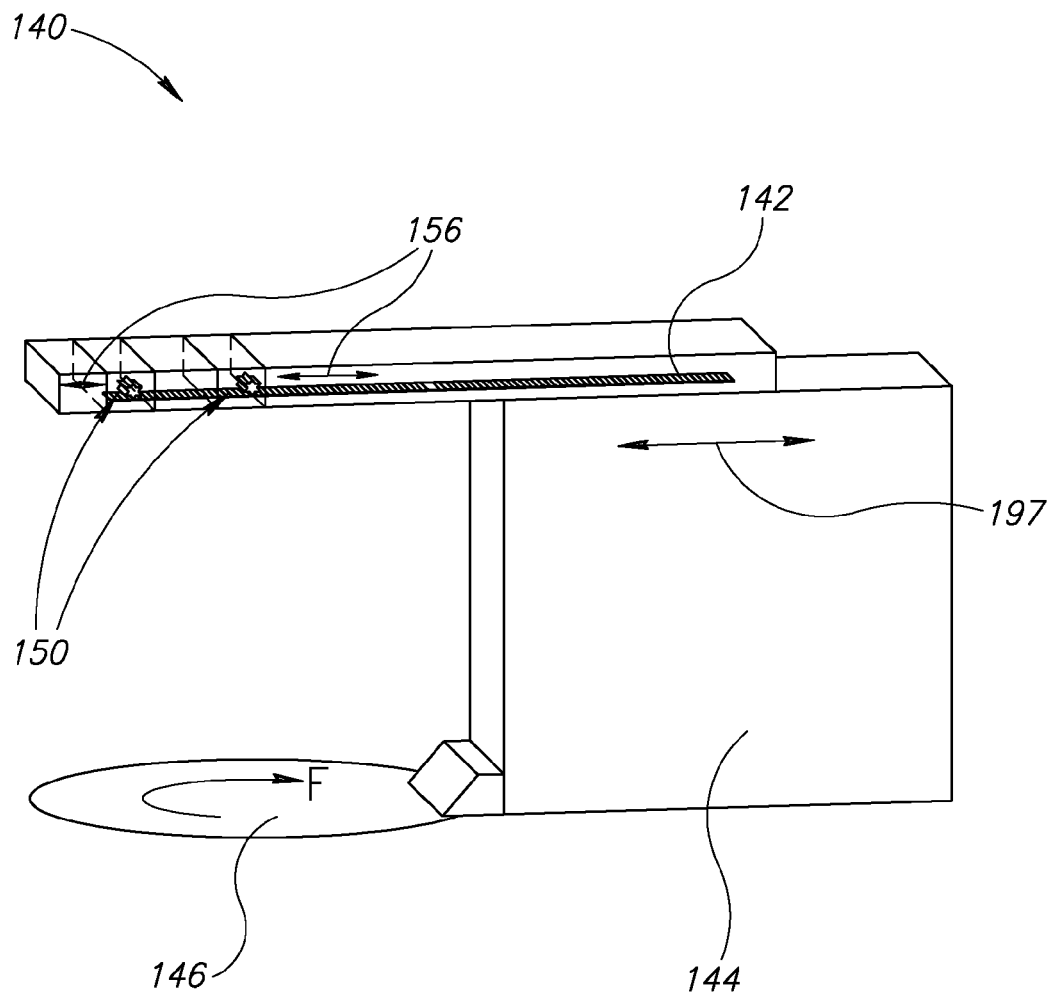

FIG. 1C depicts a patient bed 140 including moveable sensors 150 adapted for use in some exemplary embodiments of system 100. Optionally, bed 140 includes a base 144 which rotates about a standard motorized turntable 146. This arrangement permits adjustment of a patient with respect to a projected path of a cytotoxic beam.

In an exemplary embodiment of the invention, each of sensors 150 is movable, optionally independently, by a sensor displacement mechanism 156. Alternatively or additionally, platform 142 is movable by platform translation mechanism 197. Optionally, displacement mechanism 156 and/or translation mechanism 197 employ a drive mechanism such as, for example, a matched gear and toothed rail operated by a step motor. One of ordinary skill in the art will be able to construct a suitable drive mechanism from commercially available parts. Mechanisms 156 and 197 permit sensors 150 and the patient laying on platform 142 to be independently positioned at desired locations with respect to an incident radiation beam.

In an exemplary embodiment of the invention, sensors 150 are mounted in a hollow platform 142 constructed of carbon fiber. Optionally, sensors 150 roll back and forth along tracks within the shell. While linear axial tracks are shown, optionally, other shaped tracks are used, for example one or more of axial, transaxial and/or curved.

In an exemplary embodiment of the invention, the sensors are adapted to move so that they are protected from the beam by a radiation shield, for example a shield integrated into platform 142. In some cases, the shield protects the sensor from scattered radiation, rather than form direct radiation. Optionally, the shield is used in addition to moving the sensor out of the beam path. Alternatively or additionally, a separate shield element is provided (e.g., above the sensors) which is selectively moved to protect the shields. Optionally, the shield element moves on gears and tracks as shown for the sensors. Optionally, the sensor is rotated away from the beam so that its back can serve as the shield element.

A great number of commercially available platforms 142 including turntables 146 are suitable for use in the context of the invention. One example of such a platform including a turntable is Exact Couch, Varian Medical Systems; Palo Alto; CA, USA. In an exemplary embodiment of the invention, turntable 146 is controlled by system processor 180. In the pictured embodiment, turntable 146 rotates in a plane of the floor (F). Sensors 150 are optionally deployed in platform 142. In an exemplary embodiment of the invention, rotation of turntable 146 contributes to aligning a target within a patient in a desired orientation with respect to a therapeutic beam.

Optionally, platform 142 is the same width and length as standard radiation therapy couches and is 8-10 cm thick instead of the standard 5-7 cm thick. The extra thickness allows room for sensors 150 inside. In an exemplary embodiment of the invention, sensor modules 150 are 8 cm high, 45 cm wide (in direction of bed width) and 25 cm long (in direction of bed length). Optionally, rotating parts of the sensor rotate within these dimensions.

In an exemplary embodiment of the invention, platform 142 is constructed as a carbon fiber shell. Optionally, portions of the shell not occupied by sensors 150 and/or mechanism 156 and/or 197 are filled with Styrofoam. Optionally, Styrofoam filling provides added strength and/or structural integrity to platform 142. In an exemplary embodiment of the invention, platform 142 is hollow and is constructed to provide adequate strength and/or structural integrity without a Styrofoam filling.

Optionally, a 1 to 2 mm thickness of carbon fiber above and/or below sensors 150 is provided. In an exemplary embodiment of the invention, the 1 to 2 mm thickness of carbon fiber is sufficiently rigid to insulate a patient from motion of sensor 150 and/or to protect sensor 150 from patient weight.

Figure 1D:
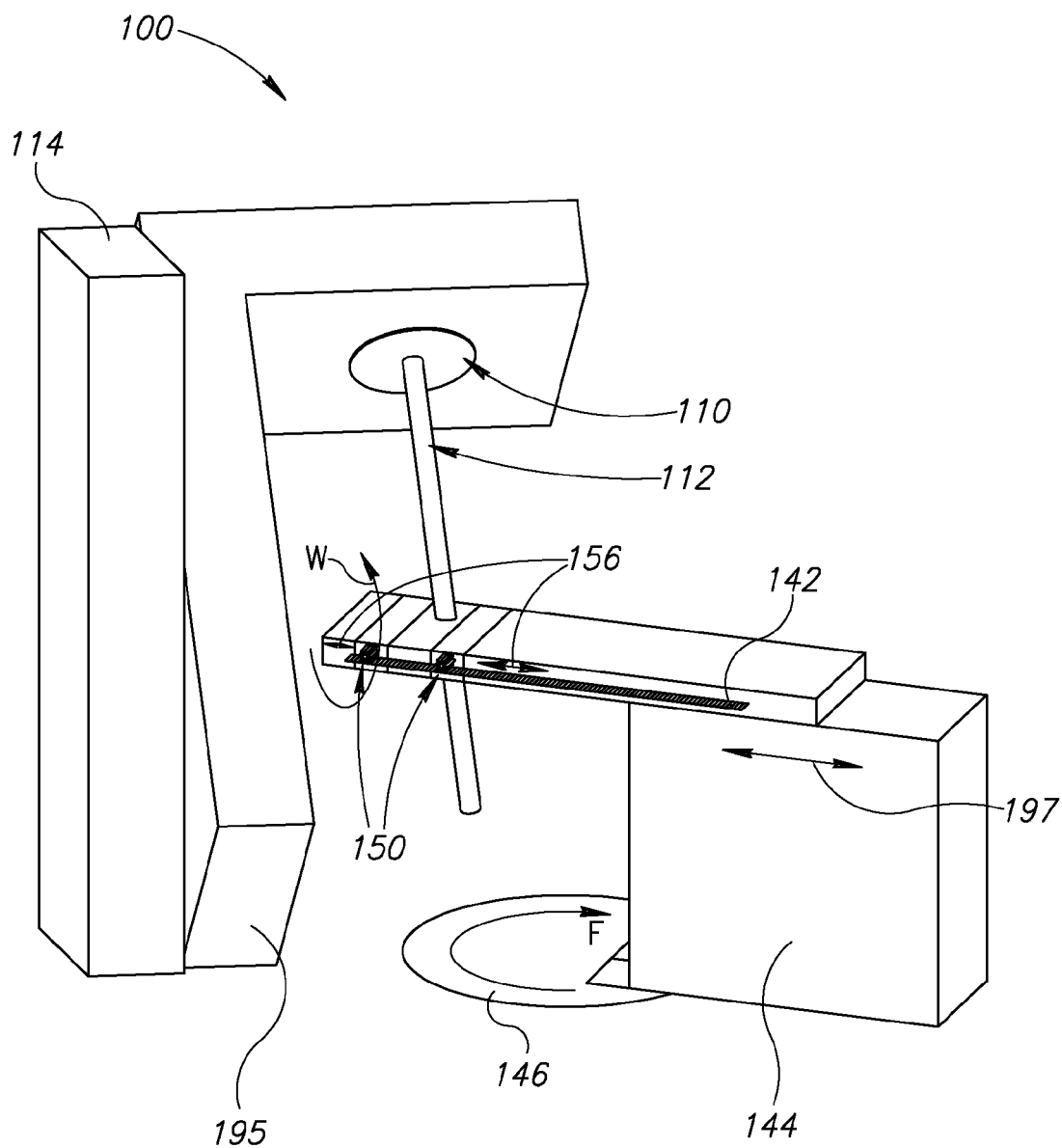

FIG. 1D depicts an exemplary system 100 including a patient bed 140 as described above together with a linear accelerator (LINAC) beam source 110 mounted on a robotic arm 195. FIG. 1D illustrates how turntable 146 and a rotation module 114 act in concert to aim beam 112 so that it passes between sensors 150.

Robotic arms are well known in the art and a large number of commercially available products exist which include a robotic arm suitable for use in the context of the invention. Arm 195 rotates in a plane of a wall (W). Rotation of arm 195 is subject to control of system processor 180 via rotation module 114. This rotation in the W plane complements rotation in the F plane provided by turntable 146.

In an exemplary embodiment of the invention, system processor 180 adjusts rotation module 114 and/or turntable 146 and/or displacement mechanisms 156 and/or 197 so that beam 112 of LINAC 110 passes between sensors 150 in platform 142.

In the depicted exemplary embodiment of the invention, sensors 150 are moved by displacement mechanisms 156 so that they are in a first position when beam 112 is operative and in a second position when beam 112 is inoperative. Optionally, this switching between two positions prevents interference with beam 112 and/or reduces scatter of energy from beam 112 and/or permits more accurate position determination of position indicator 400, optionally in tumor 130. Mechanism 197 permits beam 112 to be aimed at substantially any position on or slightly above platform 142. In an exemplary embodiment of the invention, a target 130 within subject 120 in a location determined by sensors 150 and tracking system processor 170 is used to position the target in the path of beam 112 via instructions issued from system processor 180.

In an exemplary embodiment of the invention, each of turntable 146 and rotation module 114 are independently operable to rotate through a range of ±30; ±45, ±60, ±90, or ±180 degrees or lesser or greater or intermediate amounts of rotation. Optionally, turntable 146 and rotation module 114 are each independently under the control of processor 170 and/or processor 180.

Rotation of platform 142 and/or beam source 110 is well known in the art and is described in, for example Baglan et al. (2003) Int J Radiat Oncol Biol Phys. 55(2):302-11 and Lam et al. (2001) Med Dosim. 26(1):11-5. These publications are fully incorporated herein by reference. These publications describe rotation of turntables 146 and/or rotation module 114 to avoid irradiation of non-target tissue. Calculations of appropriate angles for tissue sparing are typically performed by treatment planning software which is well known and widely available to those of ordinary skill in the art. However, standard treatment planning software does not consider the potential impact of a beam 112 on any object outside the body of a patient.

According to exemplary embodiments of the invention, system processor 180 prevents contact of beam 112 with sensors 150 using a rotation strategy similar to that employed for tissue sparing. Prevention of contact of beam 112 with sensors 150 involves altering the treatment planning software to consider the position(s) of sensor(s) 150 located outside the body. Optionally, positions of sensors 150 are adjusted using mechanisms 156 to move them out of a path of beam 112 when the beam is operative.

In an exemplary embodiment of the invention, two sensors 150 are spaced 20 cm apart so that processor 180 can aim beam 112 between them without interference. A typical therapeutic radiation beam has a width of 10 cm to 15 cm. Optionally, System processor 180 performs a series of calculations which consider displacement of platform 142, displacement of sensors 150, rotation of turntable 146, rotation of rotation module 114, position of beam source 110, and projected path of beam 112. In an exemplary embodiment of the invention, positions of sensors 150 are supplied to processor 180 as position co-ordinates which are registered with respect to target 130. Optionally, processor 180 expands the co-ordinates of sensors 150 to volumes which indicate the actual size of the sensors.

Figure 1E:
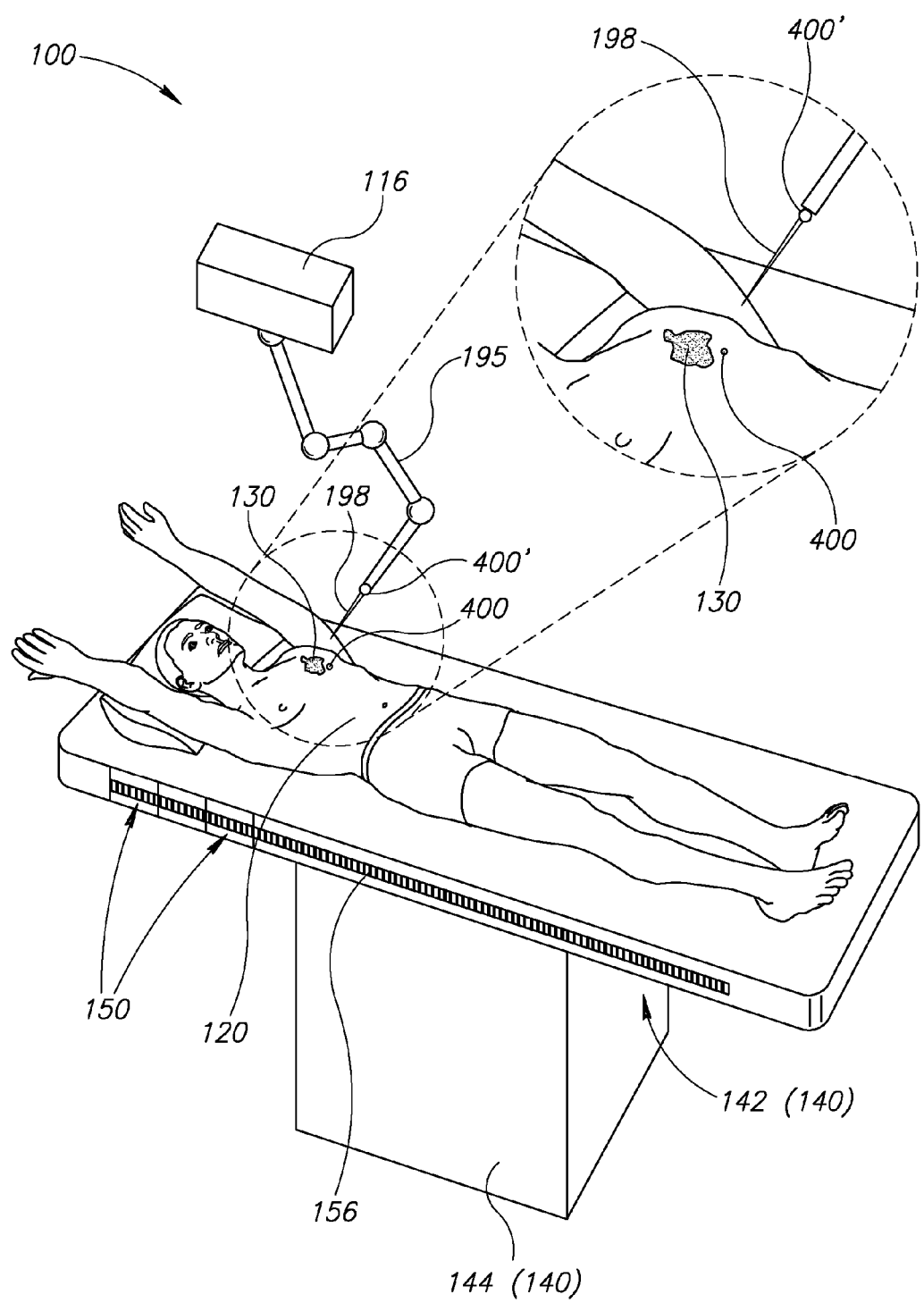
FIG. 1E is a schematic representation of a medical therapy system according to an exemplary embodiment of the invention which positions an external tool (e.g. biopsy needle)

FIG. 1E depicts an exemplary system 100 adapted for biopsy or surgical excision and including sensors 150 and an excision tool 198. Pictured exemplary system 100 includes a patient bed 140 comprising a platform 142 and base 140. For biopsy and/or excision procedures, platform 142 may be fixed with respect to base 140.

In the pictured embodiment, sensors 150 are mounted within platform and may be positioned relative to patient 120 and/or target 130 and/or position indicator 400 by means of displacement mechanism 156 as described above. Optionally, this type of arrangement permits a same bed 140 to be used for targets 130 located in different portions of patient 120.

Excision tool 198 is independently positionable with respect to target 130 and/or position indicator 400. In an exemplary embodiment of the invention, positioning of tool 198 is via a mechanism subject to control of processor 180, for example by means of a robotic arm 195 controlled by arm control unit 196. In another exemplary embodiment of the invention, tool 198 is hand-manipulated and an operator of the tool receives a signal indicating how to adjust position and/or approach angle. In an exemplary embodiment of the invention, the signal is a displayed graphic signal, for example, showing a 2D or 3D suggested trajectory and a current position and/or orientation of the tool. Optionally, a virtual 3D scene is displayed showing the target as it would be seen from a view point, for example, by a camera located on the tool. Alternatively or additionally, the signal is acoustic, for example, tones to indicate that a tool is on track and/or tones to indicate that a tool is off-track and/or a direction in which to move the tool. Optionally, the tool has attached thereto one or more LEDS or other display elements (not shown) which indicate if the tool is correctly positioned (e.g., red/green light) and/or a direction to move the tool in (e.g., 4 lights each pointing in a different direction).

In an exemplary embodiment of the invention, position indicator 400 has been implanted previously via injection. Optionally, the injection of indicator 400 has been conducted concurrently with a previous procedure, e.g. a biopsy or brachytherapy treatment.

In an exemplary embodiment of the invention, tool 198 on arm 195 is tracked by a tool tracking module which measures its position. The tool tracking module may optionally be independent of sensors 150 or rely upon sensors 150. In an exemplary embodiment of the invention, an additional position indicator 400' is applied to tool 198, optionally as a drop of glue. Other exemplary tool tracking modules can rely upon one or more of jointed mechanical tracking, flexible mechanical tracking, optical tracking, RF tracking, magnetic tracking, radioactive tracking, ultrasound tracking, inertial tracking.

In an exemplary embodiment of the invention, concurrent position determination of indicators 400 in subject 120 and 400' on tool 198 by sensors 150 aids in registering the determined positions with respect to one another Optionally, concurrent position determination of indicators 400 in subject 120 and 400' on tool 198 by sensors 150 permits tool 198 to be hand held.

In another exemplary embodiment of the invention, a position tool 198 is determined independently of sensors 150. Optionally, this permits tool 198 to be mechanically controlled. Optionally, once control unit 196 is locked at a known position, unit 196 can determine a position of tool 198 relative to itself and relay a position of tool 198 to system processor 180.

In anther exemplary embodiment of the invention, sensors 150 are physically connected to tool 198 and the tool "homes in" on indicator 400 and/or target 130. Optionally, this configuration is suitable for use with a hand held tool 198.

In an exemplary embodiment of the invention, the tool tracking module provides an output signal including a position of tool 198 to system processor 180. The output signal optionally includes or does not include an orientation of tool 198.

During a surgical procedure, system processor 180 considers the relative positions of position indicator 400 and tool 198. In an exemplary embodiment of the invention, processor 180 issues instructions to control unit 196 to adjust arm 195 so that tool 198 is brought into a desired proximity with target 130. For a needle biopsy, this proximity can vary with the length of the needle. In another exemplary embodiment of the invention, processor 180 issues instructions to a human operator holding tool 198 so that tool 198 approaches target 130. Instructions to a human operator may be issued, for example as visible signal (e.g. lighted arrows on a handle of the tool) or audible instructions. In an exemplary embodiment of the invention, the relative positions of indicator 400 and/or target 130 and tool 198 are displayed to an operator of the system. Optionally, processor 180 applies a correction which accounts for a known geometric relationship between indicator 400 and target 130 (e.g. a tumor) to determine a location of target 130 relative to tool 198. In an exemplary embodiment of the invention, the geometric relationship is known because it has been determined in advance, for example by a medical imaging procedure such as computerized tomography or fluoroscopy.

Optionally, a software tool is used to automatically determine a desired path of the tool to the target, for example, based on an identification (manual or automatic) of anatomical features that may be damaged by the tool and planning a path that bypasses them.

In some exemplary embodiments of the invention, an operator of system 100 inputs instructions to guide tool 198 to target 130. Optionally, the operator guides tool 198 by hand.

In other exemplary embodiments of the invention, system processor 180 issues instructions to arm control unit 196 so that tool 198 is guided to target 130 automatically.

In the case of a biopsy tool 198, tool control unit 196 guides tool 198 to a desired position and orientation relative to target 130. Optionally, arm 195 can be replaced by an alternate guiding mechanism, for example a gimbal.

Once biopsy tool 198 is in the desired position, a deployment command causes a biopsy needle to extend outward from tool 198 to target 130. Optionally, a sample is removed through the needle, for example by suction. Optionally, the sample is removed by withdrawing the needle. In an exemplary embodiment of the invention, positioning and deployment are based on safety considerations. For example, system processor 180 may guide tool 198 to a position which is not directly above target 130 and orient tool 198 so that a biopsy needle is ejected at a shallow angle. This can prevent the needle from penetrating into the peritoneum.

In some exemplary procedures, a position and/or orientation of tool 198 is adjusted to permit withdrawal of multiple samples from target 130. According to various exemplary embodiments of the invention, adjusting a position of tool 198 may involve altering a penetration depth of a biopsy needle and/or rotating the biopsy needle.

Optionally, a non-biopsy medical procedure is performed by tool 198 once it reaches target 130. The medical procedure may be, for example, an excision or delivery of a therapeutic agent.

In the case of an excision, tool 198 may be subject to additional manipulation after entering the body of subject 120.

In the case of delivery of a therapeutic agent, the agent may optionally be delivered at one or more positions. The positions may be reached, for example, as described above in the context of a biopsy.

Therapeutic agents include, but are not limited to, brachytherapy seeds, chemotherapeutic agents and gene therapy agents. Optionally, a brachytherapy seed may serve as a position indicator 400 after it is implanted.

In other exemplary embodiments of the invention, sensors 150 may be mounted on a robotic arm so that they can be positioned out of the way of medical personnel. Optionally, sensors 150 are mounted on a same robotic arm 195 as tool 198.

Figure 8:
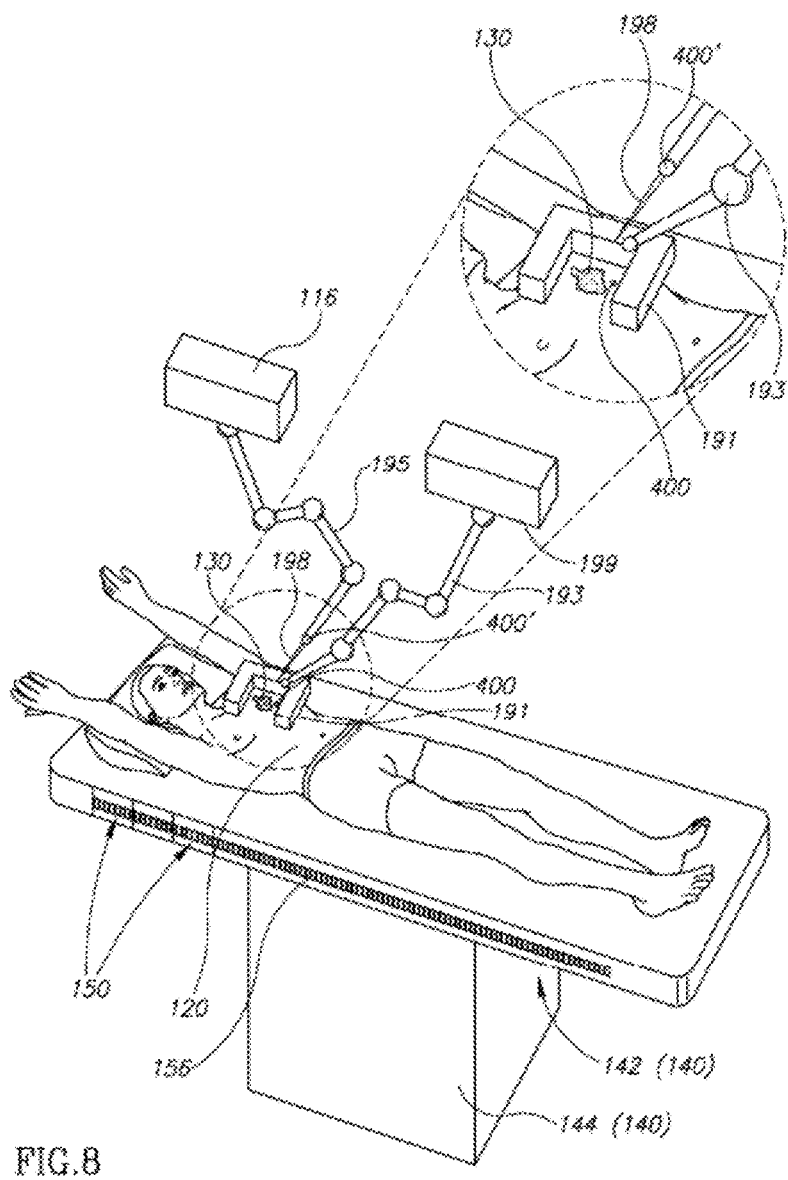
FIG. 8 is a schematic representation of a medical system including an external positionable position sensor, in accordance with an exemplary embodiment of the invention.

FIG. 8 shows an exemplary embodiment of the invention, where a separate robotic arm 193 is used to mount a sensor module 191 thereon. This may be instead of or in addition to in-bed sensors 150, shown schematically. A separate support 199 is optionally provided. Alternatively, a support 116 of arm 195 may be shared. Arm 193 optionally includes encoders or other means, so its position relative to the support is known. Optionally, the position of the support is determined by a radioactive marker mounted thereon and found by detector module 191. Optionally the position and/or orientation of the positionable position sensor module 191 relative to a given coordinate system is measured using any one of the many tracking technologies known in the art, including but not limited to magnetic, electromagnetic, optical, ultrasound and/or mechanical.

In an exemplary embodiment of the invention, module 191 is in the shape of three sides of a square. This may allow easy access from one side, or from the middle of the detector. Optionally, the module is about 50 cm in length and width and the opening is about 30-40 cm in diameter. Other open forms may be used as well. While a biopsy needle may be provided from above, in some embodiments, a tool and/or clear field of view are blocked by the sensor design. In an exemplary embodiment of the invention, sensor module 191 is placed close to the body, optionally in contact therewith, optionally from above or the side of the body. Optionally, module 191 is moved if and when it interferes with the procedure. Module 191 may then be moved back.

Figure 2:
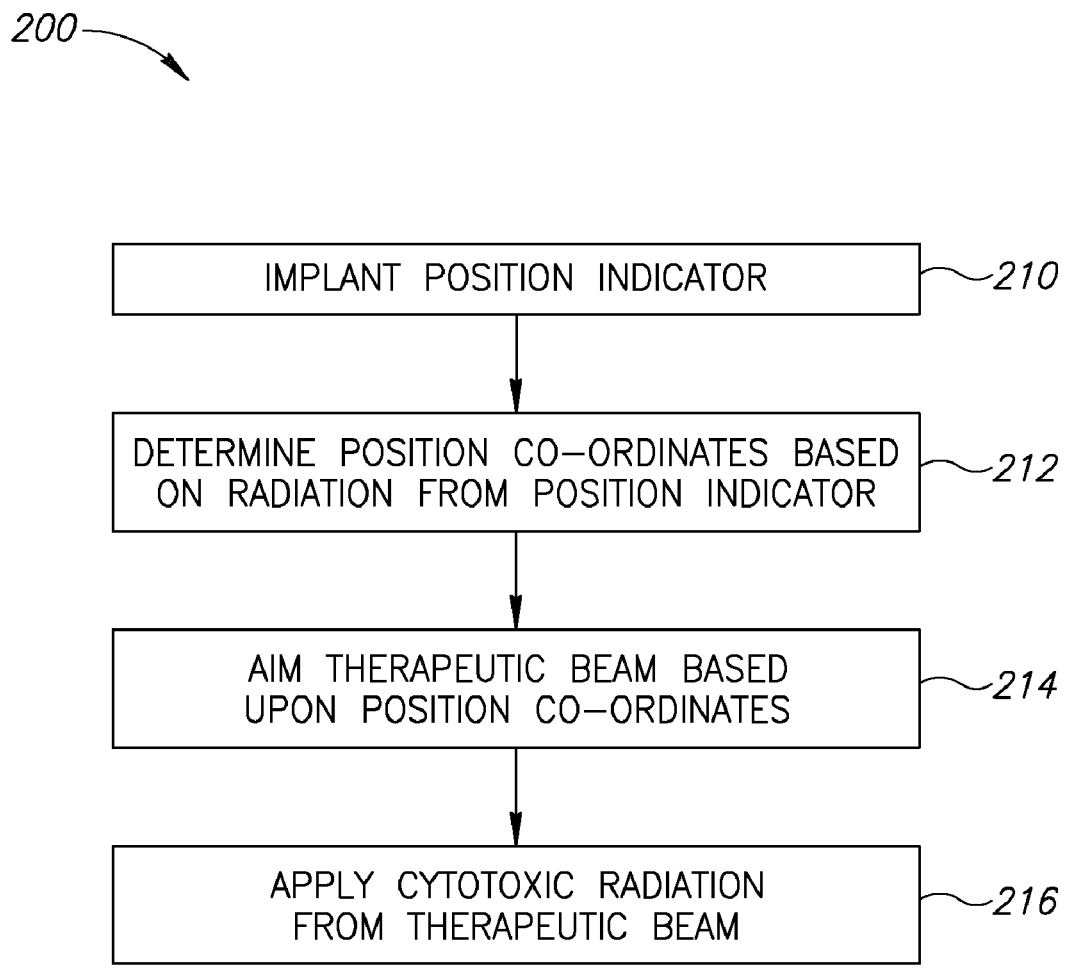
FIG. 2 is a simplified flow diagram of a therapeutic process according to an exemplary embodiment of the invention.

FIG. 2 is a simplified flow diagram of a therapeutic process 200 according to an exemplary embodiment of the invention.

At 210 a position indicator is implanted in the body of a patient. Implantation is optionally in, adjacent to, or at any known displacement with respect to a target tissue. In an exemplary embodiment of the invention, the target tissue is a tumor. The position indicator includes a radioactive source which is characterized by a desired activity, as described below.

At 212, a determination of the position co-ordinates of the position indicator is made based upon analysis of photons produced by radioactive disintegrations in the position indicator. Optionally, the analysis is made by one or more position sensors, optionally directionally sensitive position sensors.

At 214, a therapeutic beam is aimed and/or focused at an area based upon the position co-ordinates determined in 212. In an exemplary embodiment of the invention, aiming or focusing is based upon a correction which considers a known displacement between the position indicator and the target. This aiming/focusing includes registration of position coordinates employed by the location determination mechanism and co-ordinates employed by the irradiation mechanism. Registration is discussed in greater detail hereinbelow in the section entitled "Exemplary Registration Mechanisms." Optionally aiming/focusing includes moving the patient and/or moving the beam source and/or subjecting the beam source to angular adjustment. In some exemplary embodiments of the invention, 214 indicates aiming and guidance of a biopsy tool and/or ablation tool.

According to exemplary embodiments of the invention, 214 may include linear translation of a tool along tracks and/or use of gimbals and/or robotic arms and/or application of rotational motion and/or angular adjustment.

At 216, a cytotoxic dose of radiation is applied by the therapeutic beam to the area determined in 214. In some exemplary embodiments of the invention, 216 indicates performance of a biopsy and/or ablation performed by an electrode or an ultrasonic probe.

In an exemplary embodiment of the invention, 212, 214 and 216 are repeated during the course of a single treatment session. For example, if prostate tumor is to be irradiated for 120 seconds, application 216 of cytotoxic radiation might be in 10 second bursts with each burst followed by position determination 212 and focusing 214. Optionally, this type of procedure reduces the amount of radiation accidentally delivered to non-target tissue. A regimen such as this reduces the effect of involuntary shifting of relevant tissue, for example from stress and/or as a reaction to discomfort.

Figure 3:
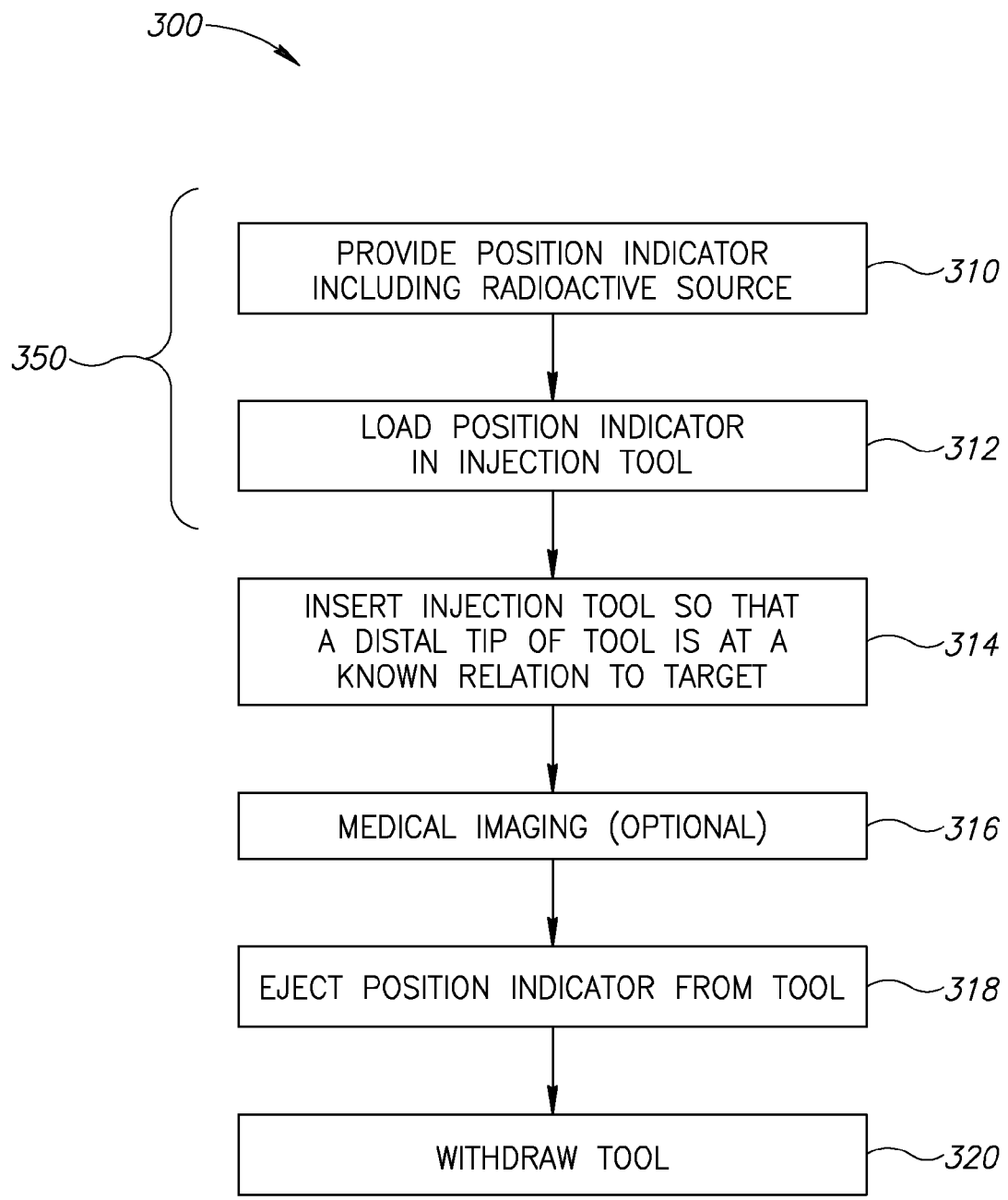
FIG. 3 is a simplified flow diagram of an implantation procedure according to an exemplary embodiment of the invention.

FIG. 3 is a simplified flow diagram of an implantation procedure 300 according to an exemplary embodiment of the invention. This diagram provides exemplary details for implantation 210 of FIG. 2.

At 310 a position indicator including a radioactive source is provided. At 312, the position indicator is loaded into an injection tool. 350 indicates that 310 and 312 may optionally be performed at a manufacturing facility so that the position indicator is provided as an individually wrapped sterilized unit loaded into an injection tool.

At 314, the injection tool is inserted so that a distal tip of the tool is at a known displacement from the target. Optionally the known displacement is small and the distal tip of the tool approaches a boundary of the target. Optionally the known displacement is essentially zero and the distal tip of the tool is within the target. In an exemplary embodiment of the invention, the distal tip of the tool approaches a center of the target.

316 indicates that insertion 314 may optionally be guided and/or evaluated by medical imaging. Guidance for placement and/or post placement evaluation of relative positions of the position indicator and the target may be conducted, for example, by ultrasound, fluoroscopy, standard X-ray imaging, CT, MRI or any other available imaging means.

At 318, the position indicator is ejected from the injection tool. Optionally, ejection is at a location which has been evaluated by imaging 316.

At 320, the injection tool is withdrawn.

Exemplary Position Indicator Configurations

Figure 4C:
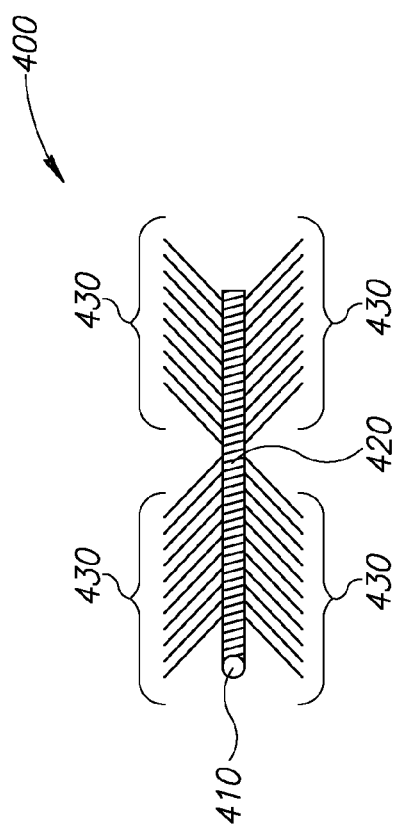

FIGS. 4A and 4C are schematic representations of position indicators according to exemplary embodiments of the invention. In the pictured exemplary embodiments, indicator 400 comprises a radioactive source 410 and a radio-opaque portion 420. Optionally, radio-opaque portion 420 serves as a fixation element. Optionally, additional anchoring structures 430 (FIG. 4C) are included. In an exemplary embodiment of the invention, indicator 400 is coated with a biocompatible coating. Optionally, the coating renders indicator 400 inert with respect to the body. In an exemplary embodiment of the invention, implantation of indicator 400 does not elicit an immune and/or inflammatory response.

An exemplary embodiment depicted in FIG. 4A illustrates a spiral configuration. Optionally, the spiral configuration serves to anchor indicator 400 in the body after it is deployed at a desired location. In an exemplary embodiment of the invention, the spiral is characterized by an elastic memory so that it tends to resume its spiral shape. In an exemplary embodiment of the figure, radio-opaque portion 420 is configured as a spiral and radioactive source 410 is concentrated at one end of indicator 400. In additional exemplary embodiments of the invention, radioactive source 410 may be concentrated in a different location with respect to the spiral or diffused along the spiral.

In an exemplary embodiment, depicted in FIG. 4C, a straight configuration is illustrated. Optionally, a herringbone pattern of filaments 430 characterized by an elastic memory serves to anchor indicator 400 in the body after it is deployed at a desired location. In the exemplary embodiment of the figure, radio-opaque portion 420 is configured as a straight cylinder and radioactive source 410 is concentrated at one end of indicator 400. In additional exemplary embodiments of the invention, radioactive source 410 may be concentrated in a different location with respect to the cylinder or diffused along the cylinder. In an exemplary embodiment of the figure, radioactive source 410 may be a radioactive coating over a non-radioactive material.

Figure 4D:
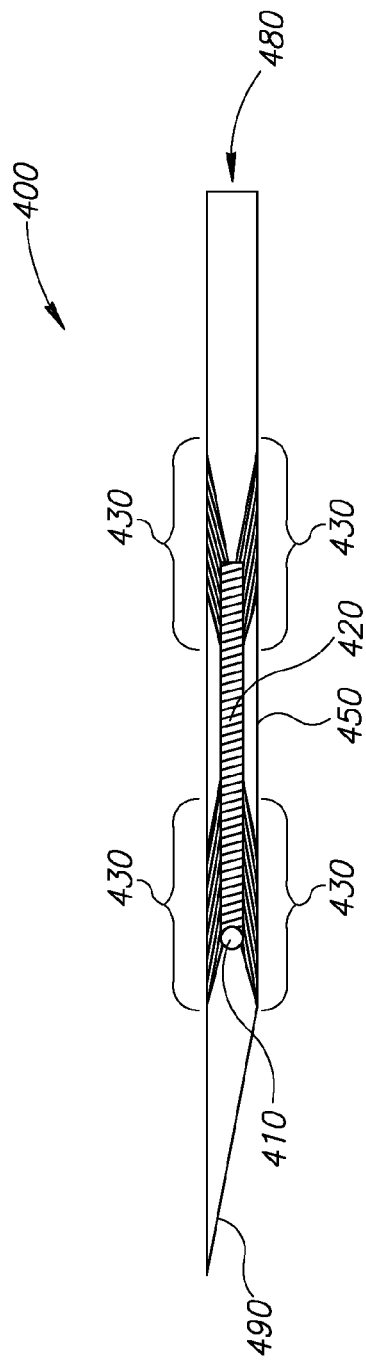

FIGS. 4B and 4D are schematic representations of the position indicators according to exemplary embodiments of the invention depicted in FIGS. 4A and 4C respectively loaded in an injection needle 450. In an exemplary embodiment of the invention, needle 450 is a standard hypodermic needle, for example a 20 to 25 gauge needle.

FIG. 4B illustrates the compression of spiral portion 420 to a kinked straight configuration within needle 450.

FIG. 4D illustrates the compression of the herringbone pattern of filaments 430 within a needle 450.

Application of an ejection force (e.g. from an inserted ejection tool) from proximal side 480 causes ejection of source 400 from distal aperture 490. Elastic memory of relevant portions of source 400 causes the ejected source to tend to revert to the relevant uncompressed configuration. In an exemplary embodiment of the invention, an ejection force is supplied by an ejection tool and/or by a stream of liquid.

In an exemplary embodiment of the invention, radioactive source 410 comprises a droplet of biocompatible glue which contains a desired radioactive isotope. Optionally, the adhesive properties of the droplet reduce a tendency to migrate or shift after injection. Optionally, the adhesive drop is contiguous and/or non-dispersing. Optionally, the droplet also includes radio-opaque material. According to this exemplary embodiment of the invention, it is source 410 itself which adheres strongly to the surrounding tissue without benefit of a separate physical anchor (e.g. spiral 420 or filaments 430). In an exemplary embodiment of the invention, a large (2-3 mm in diameter) biocompatible glue droplet, optionally including radio-opaque material can be injected through a narrow (23-25 gauge) needle since the glue is in a liquid or gel state at the time of injection. Optionally, source 410 is biodegradable and begins to lose integrity to a significant degree after 8-12 weeks. Optionally, source 410 is metabolized and the radio-isotope contained therein is excreted from the body. Optionally, the radio-isotope particles within the glue droplet are individually coated with a biocompatible material so that they remain biocompatible as the glue degrades and the particles disperse and are excreted from the body. Optionally, the glue droplet is injected in a liquid or semi-liquid state and sets to a solid mass after injection. In an exemplary embodiment of the invention, the amount of radioactivity per unit volume is adjusted according to the specific application.

Biocompatible glues suitable for use in the context of exemplary embodiments of the invention are commercially available and one of ordinary skill in the art will be able to select a suitable glue for a contemplated exemplary embodiment. Examples of biocompatible glues include, but are not limited to, Omnex (Closure Medical Corporation, Raleigh, N.C.) and BioGlue (Cryolife, Atlanta, Ga.).

According to various exemplary embodiments of the invention, the biocompatible glue may be a two-component glue (e.g. BioGlue, Cryolife, Atlanta, Ga.; USA) or a one-component glue which hardens upon contact with human tissue (e.g. Omnex, Closure Medical Corporation, Raleigh, N.C.; USA), or a glue that is hardened by the application of a transformation energy (e.g. UV light; heat; or ultrasound).

In an exemplary embodiment of the invention, a radioactive source 410 comprising a droplet of biocompatible glue which contains a desired radioactive isotope is provided as part of a kit including an injection tool. Optionally, the injection tool mixes glue components as the glue is being injected.

In an exemplary embodiment of the invention, the injection tool is a transparent syringe marked with a scale so that the amount of glue injected is readily apparent to an operator. Optionally, the scale is marked in volume and/or drop diameter. In an exemplary embodiment of the invention, there is a knob, slider, or other mechanical actuator on the injection tool which can be positioned to a certain volume or drop diameter marking which causes the appropriate amount of glue to be injected when the injection tool is activated. In an exemplary embodiment of the invention, the injection tool includes an inflatable balloon at the end of the applicator to create a space in the tissue for the bead of glue to fill. Optionally, the injection tool applies a transformation energy.

Exemplary Registration Mechanisms

In an exemplary embodiment of the invention, sensors 150 are rigidly mounted on beam source 110 or on the patient bed. According to this exemplary embodiment, a one-time calibration procedure is performed during manufacturing, installation or periodically, and the tracking and radiation systems are permanently aligned, or registered, with respect to one another.

In additional exemplary embodiments of the invention, sensors 150 are separate from the radiation therapy system. According to these exemplary embodiments of the invention, sensors 150 are registered with the radiation therapy system using an existing position and orientation determination system. Existing position and orientation determination systems include, but are not limited to, optical, ultrasound, electromagnetic and mechanical systems. A brief description of an exemplary optical tracking system useful in aligning a sensor array with a radiation therapy system can be found in "Real-time Method to Locate and Track Targets in Radiotherapy" by Kupelian and Mahadaven, Business Briefing US Oncology Review 2006, p44-46. This article is fully incorporated herein by reference. One of ordinary skill in the art will be able to select an available position and orientation determination system and incorporate it into the context of the present invention, Construction Considerations In an exemplary embodiment of the invention, a small source 410 is coupled to a relatively large position indicator 400. Optionally, use of a small source 410 (e.g. 0.5 mm to 1 mm diameter) permits sensor 150 to more accurately determine a direction from which a signal originates. Optionally, a large radio-opaque portion 420 is easily visualized in a fluorography image. In an exemplary embodiment of the invention, radio-opaque portion 420 has a length of 1, 2, 3, or 4 cm or lesser or intermediate or greater lengths. In an exemplary embodiment of the invention, radio-opaque marker 420 has a diameter compatible with injection via a 20-25 gauge OD needle.

In an exemplary embodiment of the invention, a relatively large radio-opaque portion 420 serves to anchor a smaller source 410 in position. Optionally, radio-opaque portion 420 includes a solid substrate. Anchoring should be sufficiently strong to prevent migration or shifting during at least a portion of a radiation therapy regimen, optionally through an entire radiation therapy regimen. In an exemplary embodiment of the invention, the position of indicator 400 with respect to target 130 may be measured periodically throughout the course of the radiation therapy regimen. Position of indicator 400 with respect to target 130 may be measured by, for example X-Ray, fluoroscopy, CT, MRI or ultrasound. In an exemplary embodiment of the invention, a 3D measurement of relative position is made.

In addition to or instead of the physical anchoring provided by various exemplary configurations of source 400, at least a portion of the source may be coated with a bioadhesive material. The bioadhesive material serves to fix the position of source 410 at a desired location. Examples of bioadhesives suitable for use in the context of the present invention may include, but are not limited to, cyanoacrylate based adhesives such as Omnex by Closure Medical Corporation, Raleigh, N.C. In an exemplary embodiment of the invention, the bioadhesive does not elicit an immune and/or inflammatory response.

Degree of Radioactivity

In an exemplary embodiment of the invention, indicator 400 includes a radioactive source 410 which has an activity of 300, optionally 200, optionally 100, optionally 50, optionally 25, optionally 10 µCi or intermediate or lesser values. In an exemplary embodiment of the invention, radioactive source 410 emits an amount of radiation which does not cause clinically significant cytotoxicity for 7 days, optionally 30 days, optionally 60 days, optionally 90 days or longer or intermediate times.

In the United States, there is no legal requirement to label a 10 µCi source as radioactive. A 10 µCi source, optionally concentrated in a sphere with a diameter of about 0.5 mm or less, provides $3.7 \times 10^5$ disintegrations per second. This amount of radiation is more than sufficient for a position sensor 150 to accurately determine a direction towards an origin of a received signal. In an exemplary embodiment of the invention, the degree of radiation from the source at the implantation site remains sufficiently high for position determination for a period of weeks.

Exemplary Half-Life Considerations

In an exemplary embodiment of the invention, source 410 includes Iridium ($IR^{192}$). Iridium is characterized by a half life of 73.8 days. According to exemplary embodiments of the invention, isotopes with a half life of 30, optionally 50, optionally 70, optionally 90 days or greater or intermediate or lesser half lives are included in source 410. In an exemplary embodiment of the invention, these isotopes are compatible with a radiation therapy treatment that lasts 4, optionally 6, optionally 8, optionally 10, optionally 12 weeks or lesser or intermediate or greater numbers of weeks.

For some biopsy and/or surgical procedures, for example, where the procedure is a one-time procedure and is scheduled soon after the marker implantation, relatively short half-lives can be used. Exemplary half lives can be from a few hours (e.g., 1, 4 or 20) up to days (e.g., 1, 3 or 5) or weeks (e.g., 1, 2, or 3). Intermediate, shorter or longer half lives may be provided as well.

It should be noted that for some biopsies and/or surgical procedures where the target is known to be a tumor (or other tissue) that takes up a certain radiopharmaceutical, an injected radiopharmaceutical which is taken up by the target can be used as the marker.

Safety

In an exemplary embodiment of the invention, position indicator 400 is left in place at the end of therapy. Optionally, radiation from source 410 is low enough and/or a half life of an isotope included in source 410 is short enough that there is no significant danger to the patient. In an exemplary embodiment of the invention, the non-radioactive portion of indicator 400 is constructed of biocompatible materials. Optionally, the biocompatible materials are resorbable materials.

Exemplary Position Sensor

Figure 5:
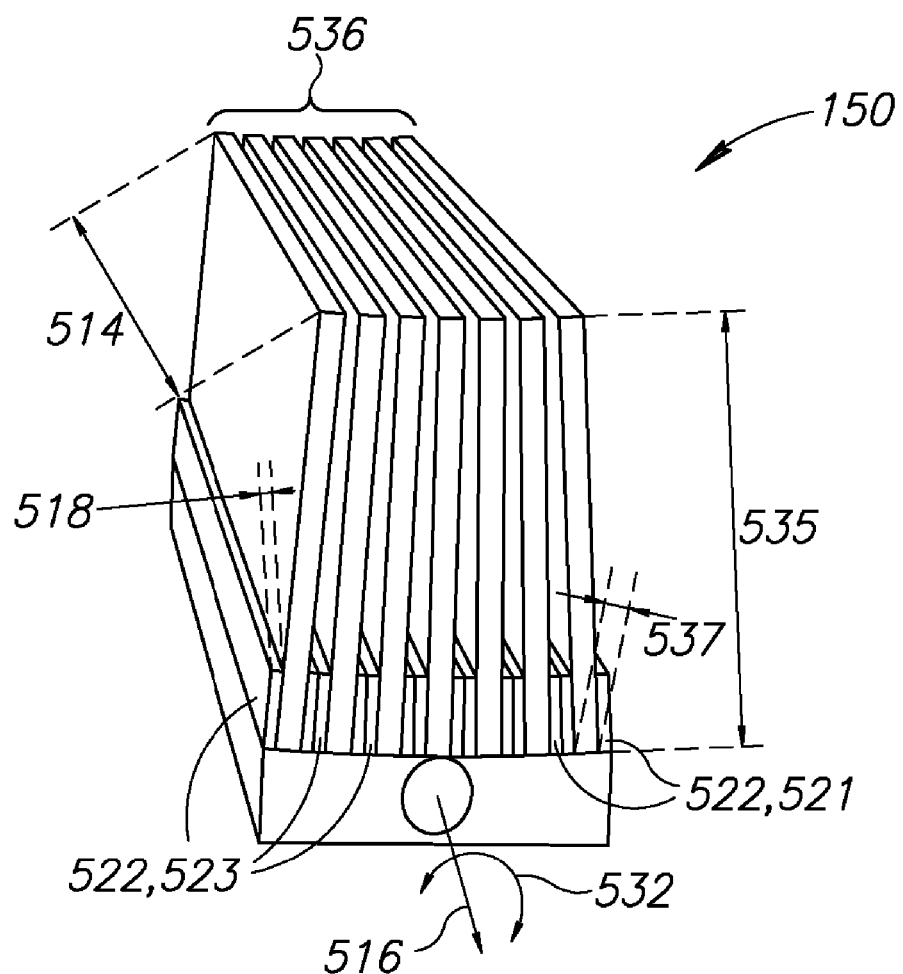
FIG. 5 is a side view of one exemplary embodiment of directional position sensor suitable for use in some exemplary embodiments of the invention.

FIG. 5 is a perspective view of one exemplary embodiment of directional position sensor 150 suitable for use in some exemplary embodiments of the invention (e.g. systems 100 as depicted in FIGS. 1A and 1B).

FIG. 5 illustrates one exemplary embodiment of a sensor 150 configured with a plurality of radiation detectors 522 and a plurality of protruding radiation shields 536 interspersed between the plurality of radiation detectors 522. In an exemplary embodiment of the invention, each detector 522 is characterized by a width 518 of 2 mm and a length 514 of 10 cm. In an exemplary embodiment of the invention, shields 536 are characterized by a height 535 of 5 cm and a width 537 at their base of 4 mm.

According to this exemplary embodiment, plurality of radiation detectors 522 is organized in pairs, each pair having a first member 521 and a second member 523. Each protruding radiation shield 536 of the plurality of protruding radiation shields is located between first member 521 and second member 523 of the pair of radiation detectors 522. According to this embodiment, sensor module 150 is capable of rotating the radiation detectors 522 through a series of rotation angles 532 about axis 516 so that receipt of radiation from a radiation source upon radiation detectors 522 varies with rotation angle 532. Each radiation detector produces an output signal.

Optionally, the output signals from all first members 521 are summed or otherwise combined to produce a first sum and the output signals from all second members 523 are summed to produce a second sum. In an exemplary embodiment of the invention, the sums are calculated by analytic circuitry. Assuming that all radiation detectors 522 are identical, when the sensor is aimed directly at the center of mass of the radiation source (target rotation angle 532), the first sum and the second sum are equivalent. Use of multiple shields 536 insures that the difference between the first sum and second sum increases rapidly with even a very slight change in rotation angle 532 in either direction. Alternately, or additionally, the sign of the total output for the entire module 150 indicates the direction of rotation required to reach the desired rotation angle 532. Optionally, sensor 150 is characterized by a rapid response time and/or a high degree of accuracy.

In an exemplary embodiment of the invention, sensor 150 is operated by implementation of an algorithm collecting gamma ray impacts from the radioactive source for a period of time and then deciding, based on a combined total output for the entire sensor 150, in which direction and to what degree to rotate radiation detectors 522 in an effort to reach a desired rotation angle 532. Optionally, the deciding is performed by analytic circuitry. Alternately an algorithm which rotate radiation detectors 522 a very small amount in response to each detected impact may be employed. Exemplary performance data is presented in PCT/IL2005/000871 the disclosure of which is fully incorporated herein by reference.

Operational Considerations

Radiation from beam source 110 of systems 100 as depicted in FIGS. 1A and 1B may potentially interfere with direction determination by sensors 150.

In an exemplary embodiment of the invention, system 100 is gated so that only output from sensors 150 provided when beam source 110 is off is considered by tracking system processor 170. Optionally, sensors 150 operate only when beam source 110 is off.

In an exemplary embodiment of the invention, sensors 150 are positioned so that they are not subject to significant reflected and/or scattered radiation from beam source 110. Optionally, sensors 150 are attached to, but at a distance from, beam source 110. In an exemplary embodiment of the invention, beam source 110 rotates about the patient 120 and/or moves freely around the patient in 3 dimensions. Optionally, once a desired relative orientation between sensors 150 and beam source 110 is established, the desired relative orientation is maintained when beam source 110 moves.

Exemplary Bioadhesive Injection Tools

Figure 6B:
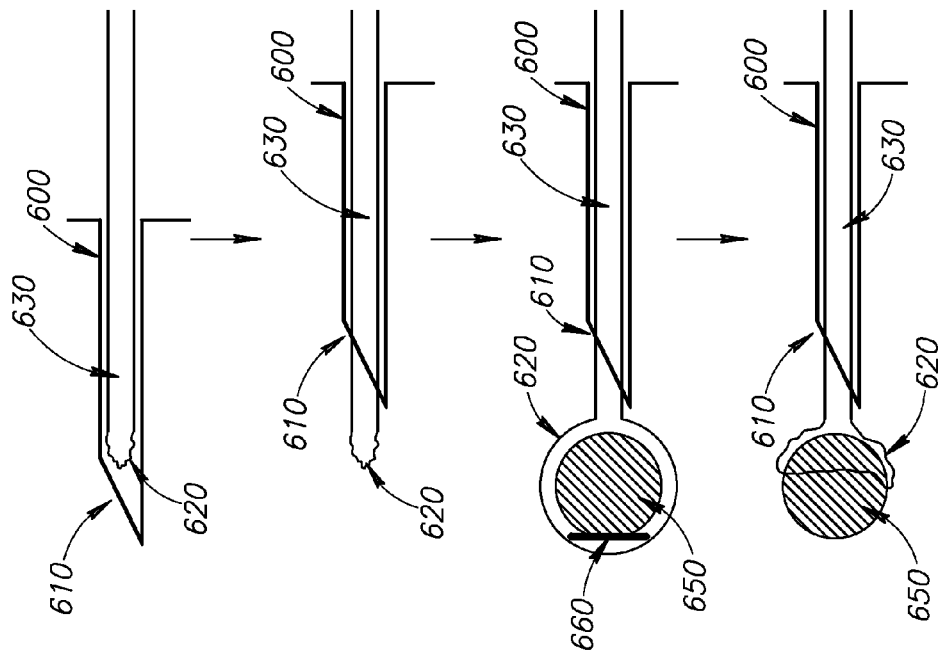
FIGS. 6A and 6B are side views of exemplary embodiments of injection tools suitable for use in injection of bioadhesive materials according to some embodiments of the invention.
Figure 6A:
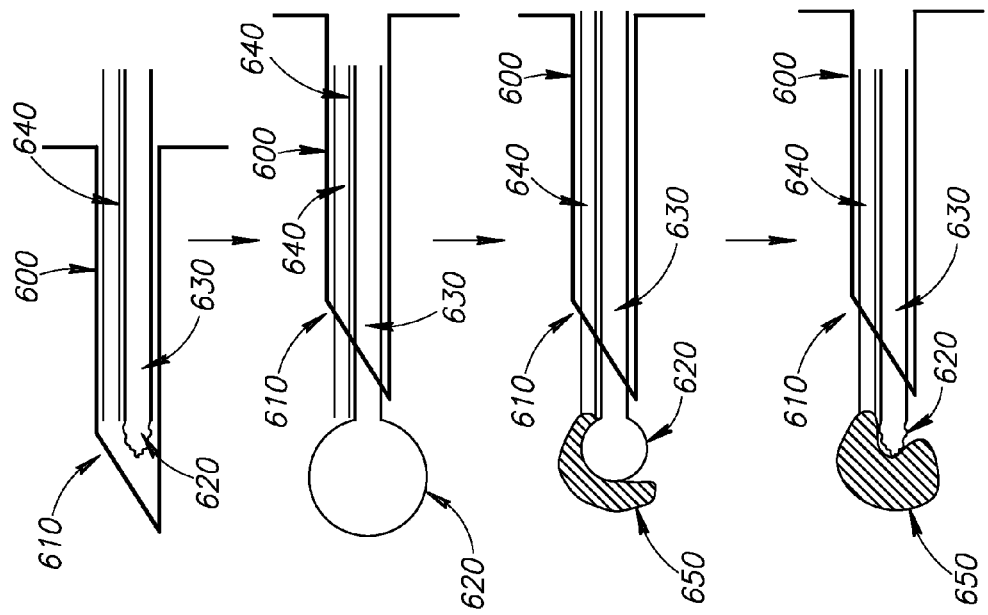

As indicated above, in some exemplary embodiments of the invention, a bioadhesive is injected through an injection tool. FIGS. 6A and 6B illustrate exemplary injection tools and their use in injecting a bioadhesive material 650. The figures illustrate exemplary sequences of events from top to bottom. In exemplary modes of use, needle 600 is inserted so that its distal end 610 is within, or at a known geometric relationship to, target 130 (FIG. 1A or 1B).

FIG. 6A illustrates one exemplary embodiment of an injection tool including two hollow tubes 630 and 640 within a needle 600. In this exemplary embodiment, tube 630 is fitted with an inflatable balloon 620 at its distal end and tube 640 is open at its distal end. Optionally, after insertion, needle 600 is retracted slightly so tubes 630 and 640 extend beyond distal end 610 of needle 600. Balloon 620 is then inflated to create a hole in tissue in or near target 130. Inflation may be, for example, with a physiologically compatible gas (e.g., oxygen, Nitrogen or an oxygen containing mixture) or a fluid (e.g. sterile saline). According to this exemplary embodiment, as balloon 620 is deflated, bioadhesive material 650 containing a radioisotope is concurrently injected through tube 640 to fill the void left by deflating balloon 620. Optionally, the radioisotope is dispersed within bioadhesive material 650. Optionally, material 650 includes a radio-opaque material. In an exemplary embodiment of the invention, partially hardened bioadhesive 650 adheres to the surrounding tissue.

FIG. 6B illustrates an additional exemplary embodiment of an injection tool which employs a single hollow tube 630 within a needle 600. The figure illustrates an exemplary sequence of events from top to bottom. In this exemplary embodiment, tube 630 is fitted with an inflatable balloon 620 at its distal end. Optionally, after insertion, needle 600 is retracted slightly so tube 630 extends beyond distal end 610 of needle 600. Balloon 620 is then inflated. In this exemplary embodiment, inflation is by filling the balloon with bioadhesive material 650 containing a radioisotope. Optionally, the radioisotope is dispersed within bioadhesive material 650. Optionally, material 650 includes a radio-opaque material.

Optionally, a wire 660 incorporated into balloon 620 is heated, optionally by an electric current. In an exemplary embodiment of the invention, heating of wire 660 melts at least a portion of balloon 620 near the wire. Optionally, this melting allows balloon 620 to be retracted into needle 600. In an exemplary embodiment of the invention, partially hardened bioadhesive 650 adheres to the surrounding tissue.

Brachytherapy Embodiments

In an exemplary embodiment of the invention, bioadhesive glue containing a radioactive isotope may be employed as a brachytherapy seed. Seeds of this type are characterized by an activity that is 10, optionally 100 or 1000 times or more or intermediate multiples greater than position indicators 400 as described hereinabove. Optionally, brachytherapy seeds of this type permit flexibility in dose localization and/or physical form of the seed. In an exemplary embodiment of the invention, use of a bioadhesive glue brachytherapy seeds permits flexible dose placement with reduced needle placements and/or facilitates use of thinner needles (e.g. 23-25 gauge). In an exemplary embodiment of the invention, bioadhesive glue brachytherapy seeds exhibit a reduced migration tendency.

Tissue Movement Modeling Embodiments

In an exemplary embodiment of the invention, a radioactive source 410 implanted within the body is used to aim a therapeutic beam 112 at a moving target. In an exemplary embodiment of the invention, sensors 150 of system 100 track source 410 along a trajectory, optionally a cyclically repeating trajectory. In an exemplary embodiment of the invention, the trajectory is relayed to system processor 180 as a series of locations, each location designated by a set of position coordinates and a temporal indicator.

According to exemplary embodiments of the invention, tracking can occur prior to therapy and/or concurrently with therapy and/or during pauses between therapeutic pulses from beam 112.

In an exemplary embodiment of the invention, acquisition of a trajectory is useful in planning therapy for a target 130 which is subject to repetitive movement (e.g. respiration or heartbeat). Optionally, after an initial trajectory is determined, sensors 150 provide additional data to processor 180 to confirm that movement of target 130 continues to match the initial trajectory and/or to indicate that target 130 has deviated from the initial trajectory. If target 130 deviates from the initial trajectory, processor 180 optionally computes a new trajectory and/or adjusts one or more of turntable 146, module 114 and mechanisms 156 and/or 197 and/or adjusts a dynamic collimator incorporated within or mounted on beam source 110 so that beam 112 coincides with target 130 without impinging on sensors 150.

In an exemplary embodiment of the invention, tissue movement modeling is employed to aim a source 110 of beam 112. As an illustrative example, a case of tumor 130 in a lung of a patient is presented in some detail. For ease of presentation, an exemplary radiation source 410 as described herein above is hypothetically implanted at a geographic center of tumor 130 (in practice source 410 and tumor 130 might be spaced apart by a known amount and a known orientation). The exemplary patient is breathing at a steady rate of twelve respirations per minute (5 seconds per respiration).

In an exemplary embodiment of the invention, prior to initiation of radiation therapy, a system 100 determines a series of locations for source 410 in a patient reclining on examination table 142 at regular time intervals, for example 0.1, 0.2, 0.5, or 1 second intervals, or greater or intermediate or smaller intervals, using position sensors 150. Optionally, system 100 continues to determine locations until analytic circuitry, e.g., processor 180 detects a repetitive pattern.

In an exemplary embodiment of the invention, positions are determined with an accuracy of 1-2 mm. Processor 180 might therefore define a pattern as repetitive if a series of points match a previous series of points with a total offset of less than 2 mm, optionally less than 1 mm. Optionally, the trajectory may be determined based upon 2, 3, 5, 10, or 20 or intermediate or greater numbers of cyclic repetitions.

In the hypothetical example under consideration, the repetitive pattern is a trajectory defined by sets of 3D position co-ordinates, each set of co-ordinates additionally defined by a time value. Once this trajectory has been ascertained, it can be employed to aim a beam 112 so that it tracks source 410 as the source 410 moves along the trajectory. Aiming of the beam 112 may be accomplished, for example, by one or more of adjusting a dynamic collimator incorporated within or mounted on beam source 110, adjusting an angle of beam source 110, adjusting a position of beam source 110 and moving a bed 142 on which the patient is positioned.

Optionally, temporal variation introduces irregularities in periodicity of the cyclically repeating trajectory. In an exemplary embodiment of the invention, positions determining the trajectory and/or breathing profiles are binned. Binning can allow processor 180 to look for secondary patterns (e.g. two short cycles followed by 1 long cycle) or drift (e.g. the y coordinate increases by 1 MM every 14 respirations).

Aiming Along the Trajectory

In an exemplary embodiment of the invention, examination table 142 and/or beam source 110 are adjusted during operation of beam 112 so that beam 112 follows the trajectory of target 130. In an exemplary embodiment of the invention, system processor 180 performs calculations for tracking based upon a known position of a center of turntable 146 and a known position of a rotation axis of rotation module 114 which are registered with respect to one another and/or with respect to a fixed co-ordinate system. Positions of sensors 150 and displacements of all system components are also registered with respect to one another and/or with respect to a fixed co-ordinate system. Once a location of source 410 is determined, it is also registered with respect to sensors 150 and/or with respect to a fixed co-ordinate system.

In an exemplary embodiment of the invention, registration of system components with respect to one another and with respect to source 110 of beam 112 permits system processor 180 to accurately aim beam 112 at target 130 and/or to adjust positions of sensors 150 so that beam 112 does not impinge upon them.

Optionally, tracking of target 130 by beam 112 and by sensors 150 occurs concurrently, optionally substantially simultaneously. In an exemplary embodiment of the invention, temporal gating is employed so that beam 112 and sensors 150 operate alternately. As the gating interval decreases, concurrent operation of beam 112 and sensors 150 approaches simultaneity.

Optionally, sensors 150 verify the position of target 130 with respect to its trajectory during therapy. Optionally, a corrected trajectory is computed if target 130 departs from the original trajectory. In an exemplary embodiment of the invention, processor 180 receives current positional information pertaining to target 130 during therapy, adjusts the trajectory in accord with the current positional information to generate a corrected trajectory and aims beam 112 according to the corrected trajectory.

In the hypothetical example described above, the therapy regimen calls for 40 seconds of radiation to be delivered to the tumor.

In an exemplary embodiment of the invention, after determination of an initial trajectory, a single 10 second pulse of radiation is delivered to the tumor from beam source 110 using an initial trajectory. At the end of the pulse, position sensors 150 are activated and send a series of temporally defined locations to processor 180. Processor 180 checks and/or re-determines and/or corrects the trajectory prior to continuation of treatment delivery of the next 10 second pulse.

In an exemplary embodiment of the invention, after determination of an initial trajectory, a 1 second pulse of radiation is delivered to the tumor from beam source 110 using the initial trajectory. At the end of the pulse, position sensors 150 are activated and send a temporally defined location to processor 180. Processor 180 checks current location against the initial trajectory and calculates a corrected trajectory if necessary prior to administering the next 1 second pulse.

In an exemplary embodiment of the invention, position sensors 150 operate while beam source 110 is in operation. Sensors 150 provide output to processor 180 which continuously corrects the trajectory as required and keeps beam 112 locked on target 130.

Temporal Gating

In an exemplary embodiment of the invention, the trajectory is used to temporally gate beam source 110 so that the beam operates only when the target is in the beam path. In the hypothetical example under consideration, the beam source might be operated with a duty cycle of one second out of five seconds with operation occurring between seconds 2 and 3 of the five second respiratory cycle.

Optionally, accuracy of tracking is related to one or more of the frequency with which 3D position co-ordinates are acquired during trajectory determination, the distance between points in the determined trajectory and the frequency with which the trajectory is verified and/or adjusted.

In an exemplary embodiment of the invention, accuracy of tracking is increased by reducing the distance between points in the determined trajectory and/or by increasing the frequency with which the trajectory is verified and/or adjusted.

In an exemplary embodiment of the invention, beam source 110 and position sensor 150 are temporally gated so that they do not operate at the same time. Optionally, temporal gating reduces interference resulting from radiation from beam source 110 impinging on position sensor 150.

The principles of target motion tracking as described above can also be applied to tool guidance as described with regard to FIG. 1E. For example, biopsy of a tumor in the abdomen by a tool 198 can be more effective if insertion of the biopsy needle is timed to consider motion of tumor 130 as a result of a respiratory cycle.

Optionally, information about the movement and trajectory of the target is provided to the user in real-time (e.g., at 0.1 Hz, 1 Hz, 10 HZ or faster) so that the needle can be selectively advanced along its path toward the target only during the portion of the target's movement cycle during which the target is in the path of the needle.

Optionally, the user uses such real-time information to identify an appropriate needle insertion path to the target when the motion is temporarily suspended during a breath hold. Optionally, the user is notified about motion stoppage using a light or audio sound associated (e.g., emanating from) with the tool.

Similar principles may be applied to other locations in the body which are subject to cyclic motion, for example the heart, by considering the amplitude and/or period of the cyclic motion.

Figure 7:
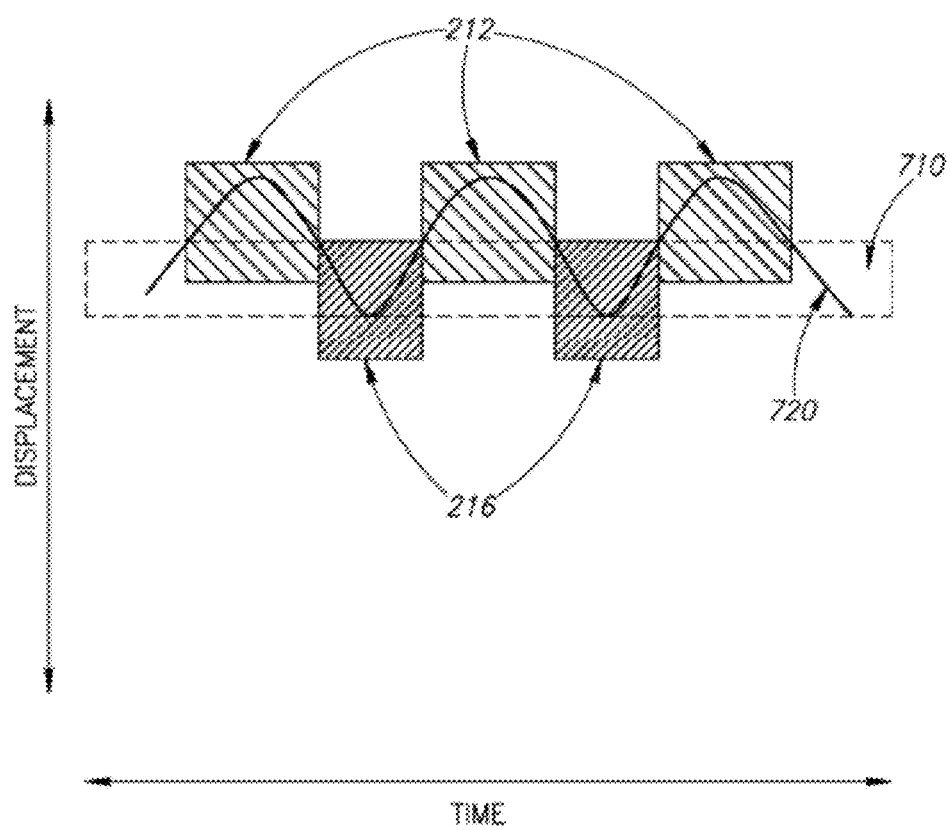
FIG. 7 is a schematic representation of temporal gating of therapy and position determination for a moving target.

FIG. 7 illustrates an exemplary trajectory 720 as a function of time. A dotted rectangle 710 indicating a path of beam 112 is superimposed on trajectory 720. In the diagram, a one dimensional trajectory is presented for clarity. However, according to exemplary embodiments of the invention, one, two, or three dimensions of trajectory 720 are measured and used in the calculations performed by processors 170 and/or 180.

As indicated by the light rectangles, position determination 212 occurs when trajectory 720 brings radiation source 410 out of the path 710 of beam 112. In an exemplary embodiment of the invention, beam 112 is shut off during these periods of time. Shutting off beam 112 reduces interference with position determination 212 and/or reduces irradiation of tissue outside of target 130.

Dark rectangles 216 indicate application of cytotoxic beam 112 to target 130 as it falls within beam path 710.

While the example presented presumes that source 410 and target 130 are co-localized, it is possible to institute temporally gated trajectory analysis based upon a source 410 at a known displacement from target 130 provided that the relative position of source 410 and target 130 does not change significantly throughout the trajectory.

General

While the textual description above has related primarily to exemplary embodiments which employ a therapeutic beam to irradiate a target, additional exemplary embodiments of the invention employ an excision or ablation tool guided in a similar manner. In an exemplary embodiment of the invention, a light beam (e.g. laser beam) is aimed in response to position co-ordinates determined as described hereinabove. The light beam indicates a site where a surgeon should open in order to perform a manual excision. In an exemplary embodiment of the invention, the tool is an imaging too, for example an ultrasonic probe.

In an exemplary embodiment of the invention, processor 180 operates displacement mechanisms 156 to remove position sensors 150 from a treatment region when not in use and/or when beam 112 is operative. Optionally, this reduces interference with treatment via beam 112 and/or reduces interference with portal imaging and/or reduces scatter.

In an exemplary embodiment of the invention, position sensors 150 are automatically positioned by processors 170 and/or 180 so that they may most accurately determine position(s) of source 410 without interfering with beam 112 emanating from beam source 110.

Optionally, LINAC 110 and an examination table are each independently rotated 30, 45 or 90 degrees or lesser or intermediate or greater numbers of degrees (e.g. by means of turntable 146 and/or rotation module 114). In an exemplary embodiment of the invention, system 100 is provided with information about an angle of the examination table 142 and an angle of LINAC 110. Optionally, this angular information is employed in calculation of a suitable location(s) for position sensors 150 so that they are not in a path of a beam 112 emanating from LINAC 110. Optionally, angular information is provided in advance by a user of system 100. Provision of angular information may be, for example from processor 180, directly by connection to LINAC 110, or via measurement.

In an exemplary embodiment of the invention, a location of radioactive source 410 is determined with an accuracy of ±5, ±2, ±1 mm or lesser or greater or intermediate accuracy. As the accuracy of individual positions increases, the accuracy and utility of a computed trajectory will increase. Determination of an accurate trajectory contributes to efficient function of processor 180 in accurately aiming of beam 112 at target 130 and/or positioning sensors 150 outside a path of beam 112.

In an exemplary embodiment of the invention, a location is determined with a 1 to 2 mm accuracy within seconds. Optionally, this rapid accurate location determination relies on one or more of a low activity source 410, one or more collimated sensors as described in WO 2006/016368 and in U.S. provisional Application 60/773,930 and the differential sensor concept described in WO 2006/016368. In an exemplary embodiment of the invention, this accuracy is an average accuracy over a tracking volume. Alternatively or additionally, the accuracy is a typical accuracy. Alternatively or additionally, the accuracy is a worst accuracy over the volume.

In some exemplary embodiments of the invention, the fact that each of sensors 150 measures only one axis permits use of slat collimators which contribute to speed and/or accuracy of location determination.

Systems 100 and/or sensors 150 and/or processor 170 and/or processor 180 may rely upon execution of various commands and analysis and translation of various data inputs. Any of these commands, analyses or translations may be accomplished by software, hardware or firmware according to various embodiments of the invention. In an exemplary embodiment of the invention, machine readable media contain instructions for registration of two independent position co-ordinate systems with respect to one another. In an exemplary embodiment of the invention, processor 170 and/or processor 180 execute instructions for registration of two independent position co-ordinate systems with respect to one another.

The word "circuitry" as used herein should be construed in its broadest possible sense so that it includes simple circuits as well as complicated electronics (e.g. a Pentium or Celeron processor) as well as mechanical circuits. The word "configured" as used may indicate "running software" or may indicate a mechanical configuration.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. Section headings are provided for ease of browsing and should not be construed to necessarily limit the contents of the sections. The scope of the invention is limited only by the following claims.

All publications and/or patents and/or product descriptions cited in this document are fully incorporated herein by reference to the same extent as if each had been individually incorporated herein by reference.

The invention claimed is:

1. A method of guiding a tool, the method comprising:
   implanting a source of radioactivity at a position having a geometric relationship to a target tissue;
   acquiring at least three sets of first and second output signals, respectively, from at least three sets of first and second radiation detectors, each set of first and second radiation detectors configured to respond to ionizing radiation from said source of radioactivity;
   determining at least three different planes in which said source of radioactivity resides using the at least three sets of first and second output signals, each plane corresponding to one set of the at least three sets of first and second output signals;
   determining at least an indication of a location of said source by calculating an intersection of the at least three different planes; and
   positioning a tool at a desired relative location with respect to said target tissue based on said determined location.

2. The method of claim 1, wherein said geometric relationship is known prior to said implanting.

3. The method of claim 1, wherein said geometric relationship is determined after said implanting using imaging.

4. The method of claim 1 comprising:
   causing at least a portion of said tool to enter the patient and approach said target tissue.

5. The method of claim 1, wherein positioning comprises maintaining said relative location while at least one of said target and said tool move.

6. The method of claim 1, wherein determining at least three different planes comprises determining a direction.

7. The method of claim 1,
   wherein a radioactivity detecting position sensor comprises at least one set of the at least three sets of first and second radiation detectors, and
   wherein said radioactivity detecting position sensor generates a direction signal using the respective set of first and second output signals.

8. The method of claim 1, wherein the positioning includes positioning directed by a positioning mechanism.

9. The method of claim 1, wherein the positioning includes manual positioning.

10. The method of claim 1 comprising:
    tracking a position of said tool.

11. The method of claim 10, wherein said tracking utilizes a non-ionizing position sensing method.

12. The method of claim 1 comprising:
    determining an orientation of said tool.

13. The method of claim 1 comprising:
    determining a relative position of said tool and said at least three sets of first and second radiation detectors.

14. The method of claim 1, wherein the determined location is defined as a relative location with respect to the target tissue.

15. The method of claim 1, wherein the source is characterized by an activity which does not cause clinically significant cytotoxicity in a period of 7 days.

16. The method of claim 1, wherein the source is selected from one of: a source attached to a fixation element and a source integrally formed with a fixation element.

17. The method of claim 1, wherein the source includes a biocompatible outer surface adapted to maintain said source in said geometrical relationship.

18. The method of claim 1, wherein the determined location is determined with an error not exceeding 2 mm.

19. The method of claim 1, wherein the determined location is determined with an error not exceeding 1 mm.

20. The method of claim 1, wherein determining at least an indication of a location comprises determining a series of indications of locations as affected by a physiological motion cycle.

21. The method of claim 20, wherein said physiological motion cycle comprises breathing.

22. The method of claim 20, wherein causing at least a portion of said tool to enter the patient is timed with respect to the physiological motion cycle.

23. The method of claim 1, wherein determining an indication of a location comprises providing a series of temporally defined locations which define a trajectory.

24. The method of claim 1, comprising:
    registering a first position coordinate system with a second position coordinate system,
    wherein the first position coordinate system is employed by the at least three sets of first and second radiation detectors and the second position coordinate system is employed by the tool.

25. The method of claim 1 comprising:
    removing at least a portion of said target tissue with said tool.

26. The method of claim 25 comprising:
    repositioning the tool at least one time and removing at least one additional portion of said target tissue.

27. The method of claim 1 comprising:
    delivering a therapeutic agent to said target tissue with said tool.

28. The method of claim 1, wherein the positioning includes moving said tool to a desired position.

29. The method of claim 1, wherein the positioning includes subjecting said tool to an angular adjustment.

30. The method of claim 1 comprising:
    supporting said patient by a frame mechanically coupled to a radioactivity detecting position sensor,
    wherein said radioactivity, detecting position sensor comprises at least one set of the at least three sets of first and second radiation detectors.

31. The method of claim 1 comprising:
    attaching a tool control unit to a frame mechanically coupled to a radioactivity detecting position sensor,
    wherein said radioactivity detecting position sensor comprises at least one set of the at least three sets of first and second radiation detectors.

32. The method of claim 1 comprising:
    providing a radioactivity detecting position sensor within a piece of furniture adapted to hold a patient during therapy,
    wherein said radioactivity detecting position sensor comprises at least one set of the at least three sets of first and second radiation detectors.

33. The method of claim 1, wherein said tool provides a light beam.

34. A therapy system, the system comprising:
    a position sensing module comprising at least three sets of first and second radiation detectors, wherein each first and second radiation detector of the at least three sets of first and second radiation detectors is
    configured to receive ionizing radiation from an implantable radioactive source, and wherein the at least three sets of first and second radiation detectors are configured to generate, respectively, at least three associated sets of first and second output signals;

a processor configured to receive and use the at least three associated sets of first and second output signals from the at least three sets of first and second radiation detectors to determine at least three different planes in which the implantable radioactive source resides, each plane of the at least three different planes corresponding to one set of the at least three associated sets of first and second output signals, the processor further configured to determine an intersection of the at least three different planes and output a position output signal;

control circuitry; and an output module;

wherein the control circuitry is configured to receive the position output signal, calculate a target location based upon the position output signal, and provide at least an indication of target coordinates to the output module; and wherein the output module is configured to receive the indication of target coordinates and assist in positioning a tool at the target location.

35. The therapy system of claim 34, wherein said output module comprises:

a tool positioning mechanism configured to position said tool with respect to said target location according to said position output signal.

36. The therapy system of claim 35, wherein said control circuitry is configured to generate said indication of target coordinates based on a desired safety effect.

37. The therapy system of claim 35, wherein said control circuitry is configured for registering a first position coordinate system with a second position coordinate system, and wherein the first position coordinate system is associated with the position sensing module and the second position coordinate system is associated with the tool positioning mechanism.

38. The therapy system of claim 35, wherein said tool positioning mechanism is configured to move said tool to a desired position.

39. The therapy system of claim 35, wherein said tool positioning mechanism is configured to subject said tool to an angular adjustment.

40. The therapy system of claim 34, wherein said output module comprises a visual display.

41. The therapy system of claim 34, wherein said control circuitry is configured to generate said indication of target coordinates based on a desired therapeutic procedure.

42. The therapy system of claim 34, wherein the position sensing module is capable of determining a position in less than 1 second and an accuracy of better than 5 mm, and wherein the implantable radioactive source is a source characterized by an activity which does not cause clinically significant cytotoxicity in a period of 7 days.

43. The therapy system of claim 42, wherein the activity is in the range of 1 µCi to 300 µCi.

44. The therapy system of claim 42, wherein the activity is in the range of 1 µCi to 100 µCi.

45. The therapy system of claim 34, wherein at least one set of the at least three sets of first and second radiation detectors comprises at least one radiation shield.

46. The therapy system of claim 45, wherein the at least one set of the at least three sets of first and second radiation detectors comprises a collimator.

47. The therapy system of claim 45, wherein the at least one set of the at least three sets of first and second radiation detectors comprises a differential radiation detector.

48. The therapy system of claim 45, wherein the at least one set of the at least three sets of first and second radiation detectors comprises a rotating radiation sensor with angular sensitivity.

49. The therapy system of claim 34, wherein the indication of target coordinates are provided with an error not exceeding 2 mm.

50. The therapy system of claim 34, wherein the indication of target coordinates are provided with an error not exceeding 1 mm.

51. The therapy system of claim 34, wherein the position output signal comprises data associated with a series of temporally defined sets of coordinates which define a trajectory.

52. The therapy system of claim 34, wherein one of the at least three sets of first and second radiation detectors is installed within a patient support adapted to hold a patient during therapy.

53. Therapy system of claim 52, wherein at least a portion of said position sensing module is positionable within said support.

54. The therapy system of claim 53, wherein at least one set of the at least three sets of first and second radiation detectors is adapted to move independently of at least one other set of the at least three sets of first and second radiation detectors.

* * * * *